US008278088B2

(12) United States Patent
Ochiai et al.

(10) Patent No.: US 8,278,088 B2
(45) Date of Patent: Oct. 2, 2012

(54) POLYNUCLEOTIDE ENCODING A POLYPEPTIDE HAVING GLYCOSYLATION ACTIVITY ON A FLAVONOID

(75) Inventors: Misa Ochiai, Osaka (JP); Harukazu Fukami, Osaka (JP); Masahiro Nakao, Osaka (JP); Akio Noguchi, Osaka (JP)

(73) Assignee: Suntory Holdings Limited, Osaka (JP)

( * ) Notice: Subject to any disclaimer, the term of this patent is extended or adjusted under 35 U.S.C. 154(b) by 0 days.

(21) Appl. No.: 12/523,068

(22) PCT Filed: Jan. 18, 2008

(86) PCT No.: PCT/JP2008/050618
§ 371 (c)(1),
(2), (4) Date: Jul. 14, 2009

(87) PCT Pub. No.: WO2008/088046
PCT Pub. Date: Jul. 24, 2008

(65) Prior Publication Data
US 2010/0273154 A1  Oct. 28, 2010

(30) Foreign Application Priority Data

Jan. 19, 2007 (JP) .................... 2007-010759

(51) Int. Cl.
| C12N 1/20 | (2006.01) |
| C12N 1/00 | (2006.01) |
| C12N 1/12 | (2006.01) |
| C12N 5/04 | (2006.01) |
| C12N 5/00 | (2006.01) |
| C12N 15/00 | (2006.01) |
| C07H 21/04 | (2006.01) |

(52) U.S. Cl. ............. 435/252.3; 435/254.11; 435/257.2; 435/419; 435/325; 435/320.1; 536/23.2; 536/23.74

(58) Field of Classification Search .................. None
See application file for complete search history.

(56) References Cited

U.S. PATENT DOCUMENTS

| 2003/0082751 A1* | 5/2003 | Okada et al. ................ 435/74 |
| 2004/0018607 A1 | 1/2004 | Callen et al. |

FOREIGN PATENT DOCUMENTS

| JP | 5-176786 | 7/1993 |
| JP | 6-277053 | 10/1994 |
| JP | 7-010897 | 1/1995 |
| JP | 8-298930 | 11/1996 |
| JP | 9-003089 | 1/1997 |
| JP | 2001-046096 | 2/2001 |
| JP | 2004-002284 | 1/2004 |
| JP | 2004-305027 | 11/2004 |
| WO | 2004-091544 | 10/2004 |
| WO | 2008/112727 | 9/2008 |

OTHER PUBLICATIONS

Dictionary definition of the term "derive", obtained from merriam-webster.com/dictionary/derive, last viewed on Mar. 2, 2011, 1 page.*
Ausubel et al., "Current Protocols in Molecular Biology", John Wiley and Sons, Inc., New York, 1993, Unit 2.10, 16 pages.*
C. Gao et al., "Novel Enzymatic Approach to the Synthesis of Flavonoid Glycosides and Their Esters" *Biotechnology and Bioengineering—Combinatorial Chemistry*, vol. 71, No. 3, pp. 235-243, 2001.
A. Noguchi et al. "A Novel Glucosylation Enzyme: Molecular Cloning, Expression, and Characterization of *Trichoderma viride* JCM22452 α-Amylase and Enzymatic Synthesis of Some Flavonoid Monoglucosides and Oligoglucosides" *Journal of Agricultural and Food Chemistry* vol. 56, No. 24, pp. 12016-12024, 2008.
Extended European Search Report issued in connection with European Application EP 08703468.2, dated Jan. 27, 2010.
Shibuya et al., "Cloning of the α-amylase cDNA of *Aspergillus shirousamii* and Its Expression in *Saccharomyces cerevisiae*", Biosci. Biotech. Biochem., vol. 56, No. 2, pp. 174-179, 1992.
Matsubara et al., "Molecular Cloning and Determination of the Nucleotide Sequence of Raw Starch Digesting α-Amylase from *Aspergillus awamori* KT-11", Journal of Biochemistry and Molecular Biology, vol. 37, No. 4, pp. 429-438, 2004.
Kometani et al., "Glucosylation of Vanillin by Cultured Plant Cells", Biosci. Biotech. Biochem., vol. 57, No. 8, pp. 1290-1293, 1993.
Funayama et al., "Enzymatic Synthesis of (+)Catechin-α-glucoside and Its Effect on Tyrosinase Activity", Biosci. Biotech. Biochem., vol. 57, No. 10, pp. 1666-1669, 1993.
GenBank_EAA63356.1, Sep. 9, 2004.
International Search Report issued in connection with PCT/JP2008/050618, mailed Feb. 12, 2008.
Kometani et al., "Shinki Haitotai no Kaihatsu ni Kansuru Kenkyu", Journal of the Japanese Society for Food Science and Technology, vol. 52, No. 3, pp. 95-101, 2005.

* cited by examiner

*Primary Examiner* — David J Steadman
(74) *Attorney, Agent, or Firm* — Greenblum & Bernstein, P.L.C.

(57) ABSTRACT

The present invention provides novel glycosyltransferase proteins produced by ascomycetous filamentous fungi (preferably species belonging to the genus *Trichoderma*, more preferably *Trichoderma viride*), as well as genes encoding the same. Among novel enzyme proteins provided by the present invention, particularly preferred is an enzyme protein obtained from the culture supernatant of *Trichoderma viride* strain IAM5141. The novel enzymes of the present invention allow glycosylation of flavonoid compounds to thereby improve their water solubility.

5 Claims, 9 Drawing Sheets

SEQUENCE LISTING

```
<160> NUMBER OF SEQ ID NOS: 33

<210> SEQ ID NO 1
<211> LENGTH: 26
<212> TYPE: DNA
<213> ORGANISM: Unknown
<220> FEATURE:
<223> OTHER INFORMATION: Description of Unknown: Ascomycetes
      sequence
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (24)..(24)
```

<223> OTHER INFORMATION: a, c, t, g, unknown or other

<400> SEQUENCE: 1
taytgyggng gnacnttyaa rggnyt                                      26

<210> SEQ ID NO 2
<211> LENGTH: 26
<212> TYPE: DNA
<213> ORGANISM: Unknown
<220> FEATURE:
<223> OTHER INFORMATION: Description of Unknown: Ascomycetes
      sequence
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other

<400> SEQUENCE: 2
ttytcnacrt gyttnacngt rtcdat                                      26

<210> SEQ ID NO 3
<211> LENGTH: 27
<212> TYPE: DNA
<213> ORGANISM: Unknown
<220> FEATURE:
<223> OTHER INFORMATION: Description of Unknown: Ascomycetes
      sequence
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 3
ggtnayrtcy tcnckrttng cnggrtc                                     27

<210> SEQ ID NO 4
<211> LENGTH: 20
<212> TYPE: DNA
<213> ORGANISM: Trichoderma viride
<220> FEATURE:
<223> OTHER INFORMATION: Strain IAM 5141

<400> SEQUENCE: 4
ccaacctggt atctacatac                                             20

<210> SEQ ID NO 5
<211> LENGTH: 19
<212> TYPE: DNA
<213> ORGANISM: Trichoderma viride
<220> FEATURE:
<223> OTHER INFORMATION: Strain IAM 5141

<400> SEQUENCE: 5
agatggcatc aaatcccat 19

<210> SEQ ID NO 6
<211> LENGTH: 2633
<212> TYPE: DNA
<213> ORGANISM: Trichoderma viride
<220> FEATURE:
<223> OTHER INFORMATION: Strain IAM 5141

<400> SEQUENCE: 6

| | | | | | |
|---|---|---|---|---|---|
| tcatacaaag | ctatttcgaa | gaccaatatt | ctacccccctt | ctccgacgat | agagccctat | 60 |
| ggtaatgggc | cgatggggttg | cttattcggc | cctttgtcgg | ccggggcatg | cgtgtttgac | 120 |
| atgttgaagc | ttgggcagat | ctgggatcgg | cgtcacggga | tgcctataac | aggaggtctg | 180 |
| taagtggctg | tttggccgcg | gcaagtttta | ttgccggagc | gaatatggcg | tctcaatgcg | 240 |
| ctacgggatc | ttgttttttgg | tctgtttggt | gtcgtttggg | caaggggggc | atatgcgata | 300 |
| tctatgccct | tggggatata | tatatatggc | ttgccgctct | ctcttccttg | gatcagcttg | 360 |
| ctgaccacag | acctcttgca | gacgcagcct | gaactcgagc | atcccacagc | tgaaagaaga | 420 |
| agatgaagct | tcgatccgcc | gtcccgctgc | tgttgcagct | ttctctcccg | gccgtccttg | 480 |
| gcgccgacac | ggcagactgg | aggtctcgta | ccatctactt | tgccctgaca | gaccgaattg | 540 |
| ctcgcagctc | aagcgacacg | ggaggctctg | cgtgtacaaa | tctgaatgac | tactgtggtg | 600 |
| gcacgttcca | gggcttggag | agcaagctgg | actacatcaa | gggcatggga | tttgatgcca | 660 |
| tctggatcaa | ccccgtcgta | accagtgagt | tgcccatcta | tccccatcct | cttgattggt | 720 |
| ggctaacatc | tcttgaaaga | cagtgatttc | ggcttccatg | gctactgggc | actggatcta | 780 |
| aacactatca | attctcacta | tggcactgcg | gatgatttaa | agagtctcgt | tgatgctgca | 840 |
| catggcaagg | tatattcaca | ccattctccc | aactgctgag | tgtcagtgct | agaaataacc | 900 |
| aaaaacaggg | cttctacatg | atggtcgacg | ttgtagccaa | ccacatggga | aacgcaaaca | 960 |
| tcacagacga | ctccccctcc | cctctgaacc | aacaatcctc | ataccacaca | aaatgtgaca | 1020 |
| ttgacttcaa | caaccagacc | agcgtcgaaa | actgttggct | tgctggcctc | ccagacgttg | 1080 |
| acacccagga | ccctaccatc | aggagcctct | accaggactg | ggtgtccaac | ctggtatcta | 1140 |
| catacggctt | cgacggcgtc | cgcatcgaca | ccgtcaggca | cgtcgagcag | gactactggc | 1200 |
| ccggcttcgt | caatgccagc | ggcgtgtact | gcatcggcga | agtcttcaac | ggagacccag | 1260 |
| actttatgca | gccctaccaa | tcgctcatgc | ccggcctcct | caactacgcc | atcttctacc | 1320 |
| ccctcaacgc | cttttatcag | cagacgggct | cctcccaagc | cctggtcgac | atgcatgacc | 1380 |
| gtctcagctc | gttcccagac | ccgacggcgc | tgggcacctt | tgtcgataac | cacgacaacc | 1440 |
| cccgcttcct | cagcgtcaag | aacgacacgt | ctctcttcaa | gaatgccctg | acctacacca | 1500 |
| ttctcggccg | aggcatcccc | attgtctact | acggctccga | gcaagccttt | tcgggaagca | 1560 |
| acgaccccgc | caacagagag | gacctctggc | gcagcggcta | caacaccgag | acggacatgt | 1620 |
| acaatgccat | ctccaagctc | acctttgcca | agcacacggc | cggcggcctc | gccgacaacg | 1680 |
| accacaagca | cctgtacgtc | gagcccacgg | catacgcctg | gagccgcgcc | ggcggcaagc | 1740 |
| tggtggcctt | taccaccaac | agcggcgcg | gcagctcggc | ccagttctgc | ttcggcacgc | 1800 |
| aggtccccaa | cgggagctgg | acgaatgtgt | ttgatggcgg | caatggcccg | acgtacactg | 1860 |
| ctgatgcgca | tggacagctc | tgcttgacca | cgacgaatgg | tgagccgatt | gtgctgctgt | 1920 |
| cttcataaaa | caatatggcg | acatataata | tacatgtata | tcacctagta | catacttgga | 1980 |

```
taggtacgtg ttacttaccc ggatagagct tcatgttgtt accttcaagc tgttgtttct    2040
ttcttctctc ttttgtggac atactgtacg atcatgaagg gtacatattt tagtcgtaac    2100
aaaattaggc atttactact acctagacta aactgtttgt tgttgatcat gtacctagag    2160
caagcaatga accatgccat gatttccttc atctcccaga cccgtatttg aattgcctgt    2220
ggatagatgt gcttgaaaga cctgccatgc gctcaaagta attgttattg aatagtccgt    2280
cccaaaatat taactgcagt gccgagatat ctgttgttcc gtcaggcctg ttcaacctgc    2340
ggggatagaa aatctccatg tgctcatgag tgcataaatt ccgcaccgaa tcctccgctt    2400
ccaaaaaaaa aaagaagca  atattataaa aagcaaagtc gtcatgccgt caaatagcct    2460
ttatagtccc gtgtatgctc gcaagtcttg tccgtcgtcg ttagcctgta ttattcacat    2520
gcgtgtgtca tcgatagcct tgtgtttctc gtgtcgcacg atttgctctt gatattgacc    2580
acattccttc ggtacaatga gcaaatatat ataccgttgt ggtgggtaat gag          2633
```

```
<210> SEQ ID NO 7
<211> LENGTH: 30
<212> TYPE: DNA
<213> ORGANISM: Trichoderma viride
<220> FEATURE:
<223> OTHER INFORMATION: Strain IAM 5141

<400> SEQUENCE: 7
ggaattcatg aagcttcgat ccgccgtccc                                       30

<210> SEQ ID NO 8
<211> LENGTH: 30
<212> TYPE: DNA
<213> ORGANISM: Trichoderma viride
<220> FEATURE:
<223> OTHER INFORMATION: Strain IAM 5141

<400> SEQUENCE: 8
ccgctcgagt tatgaagaca gcagcacaat                                       30

<210> SEQ ID NO 9
<211> LENGTH: 1392
<212> TYPE: DNA
<213> ORGANISM: Trichoderma viride
<220> FEATURE:
<223> OTHER INFORMATION: Strain IAM 5141
<220> FEATURE:
<221> NAME/KEY: CDS
<222> LOCATION: (1)..(1389)

<400> SEQUENCE: 9
```

```
atg aag ctt cga tcc gcc gtc ccg ctg ctg ttg cag ctt tct ctc ccg     48
Met Lys Leu Arg Ser Ala Val Pro Leu Leu Leu Gln Leu Ser Leu Pro
1               5                   10                  15 gcc gtc ctt ggc gcc gac acg gca gac tgg agg tct cgt acc atc tac     96
Ala Val Leu Gly Ala Asp Thr Ala Asp Trp Arg Ser Arg Thr Ile Tyr
            20                  25                  30 ttt gcc ctg aca gac cga att gct cgc agc tca agc gac acg gga ggc    144
Phe Ala Leu Thr Asp Arg Ile Ala Arg Ser Ser Ser Asp Thr Gly Gly
        35                  40                  45 tct gcg tgt aca aat ctg aat gac tac tgt ggt ggc acg ttc cag ggc    192
Ser Ala Cys Thr Asn Leu Asn Asp Tyr Cys Gly Gly Thr Phe Gln Gly
    50                  55                  60 ttg gag agc aag ctg gac tac atc aag ggc atg gga ttt gat gcc atc    240
Leu Glu Ser Lys Leu Asp Tyr Ile Lys Gly Met Gly Phe Asp Ala Ile
65                  70                  75                  80 tgg atc aac ccc gtc gta acc aac agt gat ttc ggc ttc cat ggc tac    288
```

```
                    Trp Ile Asn Pro Val Val Thr Asn Ser Asp Phe Gly Phe His Gly Tyr
                                     85                  90                  95 tgg gca ctg gat cta aac act atc aat tct cac tat ggc act gcg gat         336
Trp Ala Leu Asp Leu Asn Thr Ile Asn Ser His Tyr Gly Thr Ala Asp
                100                 105                 110 gat tta aag agt ctc gtt gat gct gca cat ggc aag ggc ttc tac atg         384
Asp Leu Lys Ser Leu Val Asp Ala Ala His Gly Lys Gly Phe Tyr Met
            115                 120                 125 atg gtc gac gtt gta gcc aac cac atg gga aac gca aac atc aca gac         432
Met Val Asp Val Val Ala Asn His Met Gly Asn Ala Asn Ile Thr Asp
    130                 135                 140 gac tcc ccc tcc cct ctg aac caa caa tcc tca tac cac aca aaa tgt         480
Asp Ser Pro Ser Pro Leu Asn Gln Gln Ser Ser Tyr His Thr Lys Cys
145                 150                 155                 160 gac att gac ttc aac aac cag acc agc gtc gaa aac tgt tgg ctt gct         528
Asp Ile Asp Phe Asn Asn Gln Thr Ser Val Glu Asn Cys Trp Leu Ala
                165                 170                 175 ggc ctc cca gac gtt gac acc cag gac cct acc atc agg agc ctc tac         576
Gly Leu Pro Asp Val Asp Thr Gln Asp Pro Thr Ile Arg Ser Leu Tyr
                180                 185                 190 cag gac tgg gtg tcc aac ctg gta tct aca tac ggc ttc gac ggc gtc         624
Gln Asp Trp Val Ser Asn Leu Val Ser Thr Tyr Gly Phe Asp Gly Val
            195                 200                 205 cgc atc gac acc gtc agg cac gtc gag cag gac tac tgg ccc ggc ttc         672
Arg Ile Asp Thr Val Arg His Val Glu Gln Asp Tyr Trp Pro Gly Phe
    210                 215                 220 gtc aat gcc agc ggc gtg tac tgc atc ggc gaa gtc ttc aac gga gac         720
Val Asn Ala Ser Gly Val Tyr Cys Ile Gly Glu Val Phe Asn Gly Asp
225                 230                 235                 240 cca gac ttt atg cag ccc tac caa tcg ctc atg ccc ggc ctc ctc aac         768
Pro Asp Phe Met Gln Pro Tyr Gln Ser Leu Met Pro Gly Leu Leu Asn
                245                 250                 255 tac gcc atc ttc tac ccc ctc aac gcc ttt tat cag cag acg ggc tcc         816
Tyr Ala Ile Phe Tyr Pro Leu Asn Ala Phe Tyr Gln Gln Thr Gly Ser
                260                 265                 270 tcc caa gcc ctg gtc gac atg cat gac cgt ctc agc tcg ttc cca gac         864
Ser Gln Ala Leu Val Asp Met His Asp Arg Leu Ser Ser Phe Pro Asp
            275                 280                 285 ccg acg gcg ctg ggc acc ttt gtc gat aac cac gac aac ccc cgc ttc         912
Pro Thr Ala Leu Gly Thr Phe Val Asp Asn His Asp Asn Pro Arg Phe
    290                 295                 300 ctc agc gtc aag aac gac acg tct ctc ttc aag aat gcc ctg acc tac         960
Leu Ser Val Lys Asn Asp Thr Ser Leu Phe Lys Asn Ala Leu Thr Tyr
305                 310                 315                 320 acc att ctc ggc cga ggc atc ccc att gtc tac tac ggc tcc gag caa        1008
Thr Ile Leu Gly Arg Gly Ile Pro Ile Val Tyr Tyr Gly Ser Glu Gln
                325                 330                 335 gcc ttt tcg gga agc aac gac ccc gcc aac aga gag gac ctc tgg cgc        1056
Ala Phe Ser Gly Ser Asn Asp Pro Ala Asn Arg Glu Asp Leu Trp Arg
                340                 345                 350 agc ggc tac aac acc gag acg gac atg tac aat gcc atc tcc aag ctc        1104
Ser Gly Tyr Asn Thr Glu Thr Asp Met Tyr Asn Ala Ile Ser Lys Leu
            355                 360                 365 acc ttt gcc aag cac acg gcc ggc ggc ctc gcc gac aac gac cac aag        1152
Thr Phe Ala Lys His Thr Ala Gly Gly Leu Ala Asp Asn Asp His Lys
    370                 375                 380 cac ctg tac gtc gag ccc acg gca tac gcc tgg agc cgc gcc ggc ggc        1200
His Leu Tyr Val Glu Pro Thr Ala Tyr Ala Trp Ser Arg Ala Gly Gly
385                 390                 395                 400 aag ctg gtg gcc ttt acc acc aac agc ggc ggc ggc agc tcg gcc cag        1248
```

```
Lys Leu Val Ala Phe Thr Thr Asn Ser Gly Gly Ser Ser Ala Gln
                405                 410                 415 ttc tgc ttc ggc acg cag gtc ccc aac ggg agc tgg acg aat gtg ttt    1296
Phe Cys Phe Gly Thr Gln Val Pro Asn Gly Ser Trp Thr Asn Val Phe
                420                 425                 430 gat ggc ggc aat ggc ccg acg tac act gct gat ggc aat gga cag ctc    1344
Asp Gly Gly Asn Gly Pro Thr Tyr Thr Ala Asp Gly Asn Gly Gln Leu
                435                 440                 445 tgc ttg acc acg acg aat ggt gag ccg att gtg ctg ctg tct tca taa    1392
Cys Leu Thr Thr Thr Asn Gly Glu Pro Ile Val Leu Leu Ser Ser
                450                 455                 460

<210> SEQ ID NO 10
<211> LENGTH: 463
<212> TYPE: PRT
<213> ORGANISM: Trichoderma viride
<220> FEATURE:
<223> OTHER INFORMATION: Strain IAM 5141

<400> SEQUENCE: 10
```

Met Lys Leu Arg Ser Ala Val Pro Leu Leu Gln Leu Ser Leu Pro
1               5                   10                  15

Ala Val Leu Gly Ala Asp Thr Ala Asp Trp Arg Ser Arg Thr Ile Tyr
                20                  25                  30

Phe Ala Leu Thr Asp Arg Ile Ala Arg Ser Ser Ser Asp Thr Gly Gly
            35                  40                  45

Ser Ala Cys Thr Asn Leu Asn Asp Tyr Cys Gly Gly Thr Phe Gln Gly
        50                  55                  60

Leu Glu Ser Lys Leu Asp Tyr Ile Lys Gly Met Gly Phe Asp Ala Ile
65              70                  75                  80

Trp Ile Asn Pro Val Val Thr Asn Ser Asp Phe Gly Phe His Gly Tyr
                85                  90                  95

Trp Ala Leu Asp Leu Asn Thr Ile Asn Ser His Tyr Gly Thr Ala Asp
            100                 105                 110

Asp Leu Lys Ser Leu Val Asp Ala Ala His Gly Lys Gly Phe Tyr Met
        115                 120                 125

Met Val Asp Val Val Ala Asn His Met Gly Asn Ala Asn Ile Thr Asp
    130                 135                 140

Asp Ser Pro Ser Pro Leu Asn Gln Gln Ser Ser Tyr His Thr Lys Cys
145                 150                 155                 160

Asp Ile Asp Phe Asn Asn Gln Thr Ser Val Glu Asn Cys Trp Leu Ala
                165                 170                 175

Gly Leu Pro Asp Val Asp Thr Gln Asp Pro Thr Ile Arg Ser Leu Tyr
            180                 185                 190

Gln Asp Trp Val Ser Asn Leu Val Ser Thr Tyr Gly Phe Asp Gly Val
        195                 200                 205

Arg Ile Asp Thr Val Arg His Val Glu Gln Asp Tyr Trp Pro Gly Phe
    210                 215                 220

Val Asn Ala Ser Gly Val Tyr Cys Ile Gly Glu Val Phe Asn Gly Asp
225                 230                 235                 240

Pro Asp Phe Met Gln Pro Tyr Gln Ser Leu Met Pro Gly Leu Leu Asn
                245                 250                 255

Tyr Ala Ile Phe Tyr Pro Leu Asn Ala Phe Tyr Gln Gln Thr Gly Ser
            260                 265                 270

Ser Gln Ala Leu Val Asp Met His Asp Arg Leu Ser Ser Phe Pro Asp
        275                 280                 285

Pro Thr Ala Leu Gly Thr Phe Val Asp Asn His Asp Asn Pro Arg Phe

```
                    290                 295                 300
Leu Ser Val Lys Asn Asp Thr Ser Leu Phe Lys Asn Ala Leu Thr Tyr
305                 310                 315                 320

Thr Ile Leu Gly Arg Gly Ile Pro Ile Val Tyr Tyr Gly Ser Glu Gln
                325                 330                 335

Ala Phe Ser Gly Ser Asn Asp Pro Ala Asn Arg Glu Asp Leu Trp Arg
                340                 345                 350

Ser Gly Tyr Asn Thr Glu Thr Asp Met Tyr Asn Ala Ile Ser Lys Leu
                355                 360                 365

Thr Phe Ala Lys His Thr Ala Gly Gly Leu Ala Asp Asn Asp His Lys
370                 375                 380

His Leu Tyr Val Glu Pro Thr Ala Tyr Ala Trp Ser Arg Ala Gly Gly
385                 390                 395                 400

Lys Leu Val Ala Phe Thr Thr Asn Ser Gly Gly Ser Ser Ala Gln
                405                 410                 415

Phe Cys Phe Gly Thr Gln Val Pro Asn Gly Ser Trp Thr Asn Val Phe
                420                 425                 430

Asp Gly Gly Asn Gly Pro Thr Tyr Thr Ala Asp Gly Asn Gly Gln Leu
                435                 440                 445

Cys Leu Thr Thr Thr Asn Gly Glu Pro Ile Val Leu Leu Ser Ser
450                 455                 460

<210> SEQ ID NO 11
<211> LENGTH: 583
<212> TYPE: DNA
<213> ORGANISM: Trichoderma reesei
<220> FEATURE:
<223> OTHER INFORMATION: Strain IFO31137

<400> SEQUENCE: 11
tggagagcaa gttggactac atcaagggca tgggatttga tgcaatctgg attacgcctg      60
ttgtgacgag tgagtttcac cttgccttgc cttgcgtcgc acaaagcctt cgggagggaa     120
taggtagctg actctgtgat acccatgggt agacagtgat ggcggctatc atggctactg     180
ggcggaggac attgactcca tcaattccca ttatggctct gcggacgact tgaagagtct     240
tgtcaatgcc gcgcatagca aggtactttc ttcccatcat cacatggctt tacccttttg     300
cgttgttcta aagcgagaga aactagggct tctatatgat ggtggatgtc gtcgccaacc     360
acatgggcta cgccaacatc accgacgata gtcctactcc tctgaaccaa gcctcttcgt     420
atcacccgga gtgtgacatc gactacaaca accagaccag cgtccaggaa tgctggatca     480
gtggtctccc ggatctcgac accgagagcc cgatgatccg cagcctctac caggactggg     540
tctccaacct cgtgtccacg tacggcttcg acggcgtccg cat                       583

<210> SEQ ID NO 12
<211> LENGTH: 592
<212> TYPE: DNA
<213> ORGANISM: Trichoderma viride
<220> FEATURE:
<223> OTHER INFORMATION: Strain IFO31327

<400> SEQUENCE: 12
tggagagcaa gttggactac atcaagggca tgggatccga tgccatctgg atcacacctg      60
ttgtgacgag tgagtctttt cataccttgc cctgccttgc ctcgcctcgc cttgcatgtg     120
tcgcatacag gcttctggta tgcatagcta aacctgatac ctctggacag acagtgatgg     180
gggctaccat ggctattggg cggaggacat cgactccatc aactctcatt atggctctgc     240
```

```
ggacgatctc aagagtctcg tcaacgccgc gcatagcaag gtattccctt ttgttcacac      300
cagacttcat gattatcaaa attaacacaa accagggctt ctatatgatg gtggacgtcg      360
tggccaacca catgggctac gccaatatct ctgacgatag tccctctcca ctgaaccagg      420
cctcgtcgta tcaccccgag tgtgatatcg actacaacag ccaaaccagc gtcgagaact      480
gctggatcag cggcctcccg gatctcaaca cgcagagctc aaccatccgc agcctctacc      540
aggactgggt ctccaacctc gtgtccacgt acggcttcga cggcgtccgc at             592
```

`<210>` SEQ ID NO 13
`<211>` LENGTH: 583
`<212>` TYPE: DNA
`<213>` ORGANISM: Trichoderma viride
`<220>` FEATURE:
`<223>` OTHER INFORMATION: Strain IFO5720

`<400>` SEQUENCE: 13

```
tggagagcaa gttggactac atcaagggca tgggattcga tgccatctgg atcacgcctg      60
ttgtgacgag tgagtctttg ccctgtcccg ccttgcctcg ggtcgtacat gggctgctag     120
agtgaacagc tgacactgat acctctgaac agacagtgat gggggctacc atggctattg     180
ggcggaggat ctcgattcca tcaactctca ctacggctct gcggatgact tgaagagtct     240
cgtcaacgcc gcacatagca aggtacttct tcctggcatg atatgacctt cgcctattct     300
cctggttcta atgcgagaca aaccagggct tctatatgat ggtagacgtc gtggccaacc     360
acatgggcta cgccaacatc tccgatgaca gccccccccc tctgaaccag gcctcttcgt     420
atcacgccga gtgtgacatt gactacaaca accagaccag cgtccagaac tgctggatca     480
gcggcctccc tgatctcgac acgcagagcc cgaccatccg cagcctctac caggactggg     540
tctccgacct cgtgtccacg tacggcttcg acggcgtccg cat                      583
```

`<210>` SEQ ID NO 14
`<211>` LENGTH: 569
`<212>` TYPE: DNA
`<213>` ORGANISM: Trichoderma viride
`<220>` FEATURE:
`<223>` OTHER INFORMATION: Strain IFO30498

`<400>` SEQUENCE: 14

```
tggagagcaa gttggactac atcaagggca tgggattcga tgccatctgg atcaccccg      60 tcgttaccag tgagttgccg acctatcccc agccaatgat atcaattcat cctcttgatt     120
aatagctaac atgccttgaa tagacagcga tttcggatac cacggttact gggctcagga     180
tattaattcc atcaattctc actatggttc ctcggatgat ttaaagagtc ttgttgatgc     240
tgctcatagc aaggtatata tttacacgac acttcaatt ttatgggtct gtgctaaacc      300
aatcaacaac agggcttcta catgatggtc gatgtcgtcg ccaaccatat gggaaacgca     360
aacatcacag acgactctcc ctctcctctg aaccaagact cctcatacca cacaaagtgt     420
gacatcgacy tcaacaacca gaccagcgtc gaaaactgtt ggctcgccgg cctcccggat     480
cttgacactc aaagccctac catcaggagc ttgtaccagg actgggtgtc caaccttgta     540
tctacatacg gcttcgacgg cgtccgcat                                      569
```

`<210>` SEQ ID NO 15
`<211>` LENGTH: 592
`<212>` TYPE: DNA
`<213>` ORGANISM: Trichoderma reesei
`<220>` FEATURE:
`<223>` OTHER INFORMATION: Strain IFO31329

```
<400> SEQUENCE: 15
tggagagcaa gttggactac atcaagggca tgggattcga tgccatctgg atcacacctg      60
ttgtgacgag tgagtctttt catacccttgc cctgccttgc ctcgcctcgc cttgcatgtg     120
tcgcatacag gcttctggta tgcatagcta aacctgatac ctctggacag acagtgatgg     180
gggctaccat ggctattggg cggaggacat cgactccatc aactctcatt atggctctgc     240
ggacgatctc aagagtctcg tcaacgccgc gcatagcaag gtattccctt ttgttcacac     300
cagacttcat gattatcaaa attaacacaa accagggctt ctatatgatg gtggacgtcg     360
tggccaacca catgggctac gccaatatct ctgacgatag tccctctcca ctgaaccagg     420
cctcgtcgta tcaccccgag tgtgatatcg actacaacaa ccaaaccagc gtcgagaact     480
gctggatcag cggccyccg gatctcaaca cgcagagctc aaccatccgc agcctctacc      540
aggactgggt ctccaacctc gtgtccacgt acggcttcga cggcgtccgc at             592

<210> SEQ ID NO 16
<211> LENGTH: 592
<212> TYPE: DNA
<213> ORGANISM: Trichoderma reesei
<220> FEATURE:
<223> OTHER INFORMATION: Strain IFO31328

<400> SEQUENCE: 16
tggagagcaa gttggactac atcaagggca tgggattcga tgccatctgg atcacacctg      60
ttgtgacgag tgagtctttt catacccttgc cctgccttgc ctcgcctcgc cttgcatgtg     120
tcgcatacag gcttctggta tgcatagcta aacctgatac ctctggacag acagtgatgg     180
gggctaccat ggctattggg cggaggacat cgactccatc aactctcatt atggctctgc     240
ggacgatctc aagagtctcg tcaacgccgc gcatagcaag gtattccctt ttgttcacac     300
cagacttcat gattatcaaa attaacacaa accagggctt ctatatgatg gtggacgtcg     360
tggccaacca catgggctac gccaatatct ctgacgatag tccctctcca ctgaaccagg     420
cctcgtcgta tcaccccgag tgtgatatcg actacaacaa ccaaaccagc gtcgagaact     480
gctggatcag cggcctcccg gatctcaaca cgcagagctc aaccatccgc agcctctacc     540
aggactgggt ctccaacctc gtgtccacgt acggcttcga cggcgtccgc at             592

<210> SEQ ID NO 17
<211> LENGTH: 592
<212> TYPE: DNA
<213> ORGANISM: Trichoderma reesei
<220> FEATURE:
<223> OTHER INFORMATION: Strain IFO31326

<400> SEQUENCE: 17
tggagagcaa gttggactac atcaagggca tgggattcga tgccatctgg atcacacctg      60
ttgtgacgag tgagtctttt catacccttgc cctgccttgc ctcgcctcgc cttgcatgtg     120
tcgcatacag gcttctggta tgcatagcta aacctgatac ctytggacag acagtgatgg     180
gggctaccat ggctattggg cggaggacat cgactccatc aactctcatt atggctctgc     240
ggacgatctc aagagtctcg tcaacgccgc gcatagcaag gtattccctt ttgttcacac     300
cagacttcat gattatcaaa attaacacaa accagggctt ctatatgatg gtggacgtcg     360
tggccaacca catgggctac gccaatatct ctgacgatag tccctctcca ctgaaccagg     420
cctcgtcgta tcaccccgag tgtgatatcg actacaacaa ccaaaccagc gtcgagaact     480
gctggatcag cggcctcccg gatctcaaca cgcagagctc aaccatccgc agcctctacc     540
```
aggactgggt ctccaacctc gtgtccacgt acggcttcga cggcgtccgc at        592

<210> SEQ ID NO 18
<211> LENGTH: 583
<212> TYPE: DNA
<213> ORGANISM: Trichoderma koningii
<220> FEATURE:
<223> OTHER INFORMATION: Strain IAM12534

<400> SEQUENCE: 18
tggagagcaa gttggactac atcaagggca tgggattcga tgccatctgg atcacgcctg     60
ttgtgacgag tgagtctttg ccctgtcccg ccttgcctcg ggtcgtacat gggctgctag    120
agtgaacagc tgacactgat acctctgaac agacagtgat gggggctacc atggctattg    180
ggcggaggat ctcgattcca tcaactctca ctacggctct gcggatgact tgaagagtct    240
cgtcaacgcc gcacatagca aggtacttct tcctggcatg atatgacctt cgcctattct    300
cctggttcta acgcgagaca aaccaggget tctatatgat ggtagacgtc gtggccaacc    360
acatgggcta cgccaacatc tccgatgaca gccctccccc tctgaaccag gcctcttcgt    420
atcacgccga gtgtgacatt gactacaaca accagaccag cgtccagaac tgctggatca    480
gcggcctccc tgatctcgac acgcagagcc cgaccatccg cagcctctac caggactggg    540
tctccaacct cgtgtccacg tacggcttcg acggcgtccg cat                     583

<210> SEQ ID NO 19
<211> LENGTH: 584
<212> TYPE: DNA
<213> ORGANISM: Trichoderma viride
<220> FEATURE:
<223> OTHER INFORMATION: Strain SAM1427

<400> SEQUENCE: 19
tggagagcaa gttggactac atcaagggca tgggatttga tgccatctgg atcactcctg     60
ttgtgacgag tgagttttcac cttgccttgc cttgcgtcgc acaaagcctt cgagagggaa   120
taggtagctg actctgtgat acccatgggt agacagtgat ggcggctatc atggctactg    180
ggcggaggac attgactcca tcaattccca ttatggctct gcagacgact tgaagagtct    240
tgtcaatgcc gcgcatagca aggtattttc ttcccagcat tggtttgatg tttgcccctt    300
tggcattatt ctcaagcaag aaaccagggc ttctatatga tggtggatgt cgtcgccaac    360
catatgggct acgccaacat caccgacgat agtcctactc ctctgaacca agcctcttcg    420
tatcacccgg agtgtgacat cgactacagc aaccagacca gcgtccagga atgctggatc    480
agcggcctcc cggatctcga caccgagagc ccgacgatcc gcagcctcta ccaggactgg    540
gtctccaatc tcgtgtccac gtacggcttc gacggcgtcc gcat                    584

<210> SEQ ID NO 20
<211> LENGTH: 614
<212> TYPE: DNA
<213> ORGANISM: Trichoderma ghanense
<220> FEATURE:
<223> OTHER INFORMATION: Strain IAM13109

<400> SEQUENCE: 20
tggagagcaa gttggactac atcaagggca tgggattcga tgccatctgg atcacccctg     60
ttgtgacgag tgagtctttt gccttgcctt gccttgcctt gccttgcctt gccttgcctt    120
rccttgcctt gtgtcgcaca caggctcctg gaggaaatgg ctgatgctga taccttggaa    180
tagacagtga tgggggttat catggctatt gggcggagga cattgattcc atcaactctc    240

-continued

```
attacggctc tgcggacgac ctgaagagtc tcgtcaatgc cgcgcatagc aaggtacatc    300
tccccatcat tgacataggt ttacccttt gcatgattct gacgtgagac aaaccagggc    360
ttctatatga tggtggacgt cgtggccaac cacatgggct acgccaacat ctccgacgac    420
agtccttctc ctctgaacca agcgtcgtcc tatcacccag agtgtgacat tgactacaac    480
aaccagacca gcgtccagaa ctgctggatc agcggcctcc cggatctcaa cacgcagagc    540
tcgacgatcc gcagcctcta ccagggctgg gtctccgacc tcgtgtccac ctacggcttc    600
gacggcgtcc gcat                                                      614
```

<210> SEQ ID NO 21
<211> LENGTH: 572
<212> TYPE: DNA
<213> ORGANISM: Trichoderma saturnisporum
<220> FEATURE:
<223> OTHER INFORMATION: Strain IAM12535
<220> FEATURE:
<221> NAME/KEY: modified_base
<222> LOCATION: (445)..(445)
<223> OTHER INFORMATION: a, c, g, t, unknown or other

<400> SEQUENCE: 21

```
tggagagcaa gctggactac atcaagggca tgggattcga tgccatctgg atcacgcctg     60
ttgtgacgag tgagtctttg attaccttgt gtcgcacaca gtcttataga ggagatggat    120
cacactgaca tgtccggata gacagtcagg ggggctacca wggctactgg gcagaggaca    180
ttgactccat caattctcat tacggctctg cggacgacct gaagagtctc gtcaatgccg    240
cgcatagcaa ggtacttctt cctctcattg acatgccttt attcctttcg cgttgtccta    300
aaccgagatt tacagggctt ctatatgatg gtggatgtcg tcgccaacca catgggcaac    360
gccaacatct ccgacgatag tcctcctcct ctgaacgaag cctcttcgta tcaccccag    420 tgtgacattg actacaacaa ccamnccagc gtccagaact gctggatcag cggcctcccg    480
gatctcaaca cccagagctc gacgatccgc agcctctacc aggactgggt ccacaacctc    540
gtgtcgacgt acggcttcga cggcgtccgc at                                  572
```

<210> SEQ ID NO 22
<211> LENGTH: 572
<212> TYPE: DNA
<213> ORGANISM: Trichoderma polysporum
<220> FEATURE:
<223> OTHER INFORMATION: Strain SAM357

<400> SEQUENCE: 22

```
tggagggcaa gttggattac atcaagggga tgggatttga tgctatttgg atcacgcctg     60
ttgtaacgag taagttattc ataacagcct cagatatcat ctcctgggtc aatagctaat    120
atatcttgat agatagcgat caggggtatc atggctactg ggcagaggat ctcgattcta    180
tcaattctca ctatggttct tcggatgatt tgaagagtct tgtcgatgct gcacacagca    240
aggtacgtca tatcacctca cccccctaca ttctgctaat cctcatggat cgtgctaaac    300
cgaatgttaa ataggggctt ctatatgatg gtcgatgttg ttgccaatca catgggatat    360
gcaaacatca ccgacgacct tcccactcct ctaaaccaaa actcgtctta ccacgcagag    420
tgtaacatcg actataacaa tcagaccagc gtcgaaaact gctggatcga tggtctccca    480
gaccttgaca cacagagcga gactatccgc acccttaca aggactgggt ttccaacctc    540
gtctccacat acggcttcga cggcgtccgc at                                  572
```

<210> SEQ ID NO 23

```
<211> LENGTH: 571
<212> TYPE: DNA
<213> ORGANISM: Trichoderma reesei
<220> FEATURE:
<223> OTHER INFORMATION: Strain IFO31292

<400> SEQUENCE: 23 tgagggcaa gttggactac atcaagggca tgggattcga cgccatctgg atcacgcccg    60
tcgttacgag tgagttacac acagcctcag gcattacctc ttgaatgcgc ttctaatgtt   120
aatatttaaa tagatagcga cgggggggtac cacggttact gggctgagtc tctggattcg   180
atcaattctc attatggttc tgcggatgat ttaaagagtc tcgttgatgc tgcgcatagc   240
aaggtacgtg atactccaca ccccatctta tatgcctcta ttttcgaagt acggtgctaa   300
aaaggtgaaa acagggtttc tatatgatgg tagatgttgt tgccaatcat atgggttatg   360
ccaacatttc tgacgacctc ccaactcccc tgaacgaaaa ctcgtcgtat catccagaat   420
gcgacattga ctacaacaac cagaccagcg tcgaaaactg ctggatcgat ggccttccgg   480
atctcgacac tcagagccct accatccgca gcctctacca ggactgggtc tccaacctcg   540
tatcgaccta cggcttcgac ggcgtccgca t                                   571

<210> SEQ ID NO 24
<211> LENGTH: 572
<212> TYPE: DNA
<213> ORGANISM: Trichoderma hamatum
<220> FEATURE:
<223> OTHER INFORMATION: Strain IAM12505

<400> SEQUENCE: 24
tggagagcaa gttggactat atcaagggca tgggatttga cgccatctgg atcacgcccg    60
tcgttacgag tgagttatat acagcctcac acattatccc ttcaaagagc atctaatatt   120
tatatttaaa tagacagtga taagggctat cacggctact gggcagaaga tatcgattct   180
attaattctc actatggttc tgcggacgat ttaaagagtc tcgtcgatgc tgcgcatagc   240
aaggtacatc atacgcaaca ccccatctta tatgcctcta ctctcgaaat gtcctgctaa   300
aacaagtgaa acagggctt ctacatgatg gtagatgttg tcgccaatca tatgggctat    360
gccaatattc ctgacgacct tccaaccccc tgaacgaga actcgtcgta tcacccggaa   420
tgcgacattg actacaacaa cgagaccagc gtcgaaaact gctggatcag cggtctcccc   480
gatctcgaca cccagagccc taccatccgc agtctctacc aggactgggt ctccaacctc   540
gtctcgacct acggcttcga cggcgtccgc at                                 572

<210> SEQ ID NO 25
<211> LENGTH: 1329
<212> TYPE: DNA
<213> ORGANISM: Trichoderma viride
<220> FEATURE:
<223> OTHER INFORMATION: Strain IAM 5141

<400> SEQUENCE: 25
gccgacacgg cagactggag gtctcgtacc atctactttg ccctgacaga ccgaattgct    60
cgcagctcaa gcgacacggg aggctctgcg tgtacaaatc tgaatgacta ctgtggtggc   120
acgttccagg gcttggagag caagctggac tacatcaagg gcatgggatt tgatgccatc   180
tggatcaacc ccgtcgtaac caacagtgat ttcggcttcc atggctactg gcactggat    240 ctaaacacta tcaattctca ctatggcact gcggatgatt taaagagtct cgttgatgct   300
gcacatggca agggcttcta catgatggtc gacgttgtag ccaaccacat gggaaacgca   360
```

```
aacatcacag acgactcccc ctcccctctg aaccaacaat cctcatacca cacaaaatgt    420
gacattgact tcaacaacca gaccagcgtc gaaaactgtt ggcttgctgg cctcccagac    480
gttgacaccc aggaccctac catcaggagc ctctaccagg actgggtgtc caacctggta    540
tctatatacg gcttcgacgg cgtccgcatc gacaccgtca ggcacgtcga gcaggactac    600
tggcccggct tcgtcaatgc cagcggcgtg tactgcatcg gcgaagtctt caacggagac    660
ccagacttta tgcagcccta ccaatcgctc atgcccggcc tcctcaacta cgccatcttc    720 tacccccctca acgccttttta tcagcagacg ggctcctccc aagccctggt cgacatgcat    780
gaccgtctca gctcgttccc agacccgacg gcgctgggca cctttgtcga taaccacgac    840 aaccccgct tcctcagcgt caagaacgac acgtctctct tcaagaatgc cctgacctac    900
accattctcg gccgaggcat ccccattgtc tactacggct ccgagcaagc cttttcggga    960
agcaacgacc ccgccaacag agaggacctc tggcgcagcg gctacaacac cgagacggac   1020
atgtacaatg ccatctccaa gctcaccttt gccaagcaca cggccggcgg cctcgccgac   1080
aacgaccaca gcacctgta cgtcgagccc acggcatacg cctggagccg cgccggcggc   1140
aagctggtgg cctttaccac caacagcggc ggcggcagct cggcccagtt ctgcttcggc   1200
acgcaggtcc ccaacgggag ctggacgaat gtgtttgatg gcggcaatgg cccgacgtac   1260
actgctgatg gcaatggaca gctctgcttg accacgacga atggtgagcc gattgtgctg   1320
ctgtcttca                                                            1329
```

<210> SEQ ID NO 26
<211> LENGTH: 443
<212> TYPE: PRT
<213> ORGANISM: Trichoderma viride
<220> FEATURE:
<223> OTHER INFORMATION: Strain IAM 5141

<400> SEQUENCE: 26

```
Ala Asp Thr Ala Asp Trp Arg Ser Arg Thr Ile Tyr Phe Ala Leu Thr
1               5                   10                  15

Asp Arg Ile Ala Arg Ser Ser Ser Asp Thr Gly Gly Ser Ala Cys Thr
            20                  25                  30

Asn Leu Asn Asp Tyr Cys Gly Gly Thr Phe Gln Gly Leu Glu Ser Lys
        35                  40                  45

Leu Asp Tyr Ile Lys Gly Met Gly Phe Asp Ala Ile Trp Ile Asn Pro
    50                  55                  60

Val Val Thr Asn Ser Asp Phe Gly Phe His Gly Tyr Trp Ala Leu Asp
65                  70                  75                  80

Leu Asn Thr Ile Asn Ser His Tyr Gly Thr Ala Asp Asp Leu Lys Ser
                85                  90                  95

Leu Val Asp Ala Ala His Gly Lys Gly Phe Tyr Met Met Val Asp Val
            100                 105                 110

Val Ala Asn His Met Gly Asn Ala Asn Ile Thr Asp Asp Ser Pro Ser
        115                 120                 125

Pro Leu Asn Gln Gln Ser Ser Tyr His Thr Lys Cys Asp Ile Asp Phe
    130                 135                 140

Asn Asn Gln Thr Ser Val Glu Asn Cys Trp Leu Ala Gly Leu Pro Asp
145                 150                 155                 160

Val Asp Thr Gln Asp Pro Thr Ile Arg Ser Leu Tyr Gln Asp Trp Val
                165                 170                 175

Ser Asn Leu Val Ser Thr Tyr Gly Phe Asp Gly Val Arg Ile Asp Thr
            180                 185                 190
```

```
Val Arg His Val Glu Gln Asp Tyr Trp Pro Gly Phe Val Asn Ala Ser
        195                 200                 205

Gly Val Tyr Cys Ile Gly Glu Val Phe Asn Gly Pro Asp Phe Met
    210                 215                 220

Gln Pro Tyr Gln Ser Leu Met Pro Gly Leu Leu Asn Tyr Ala Ile Phe
225                 230                 235                 240

Tyr Pro Leu Asn Ala Phe Tyr Gln Gln Thr Gly Ser Ser Gln Ala Leu
            245                 250                 255

Val Asp Met His Asp Arg Leu Ser Ser Phe Pro Asp Pro Thr Ala Leu
                260                 265                 270

Gly Thr Phe Val Asp Asn His Asp Asn Pro Arg Phe Leu Ser Val Lys
        275                 280                 285

Asn Asp Thr Ser Leu Phe Lys Asn Ala Leu Thr Tyr Thr Ile Leu Gly
290                 295                 300

Arg Gly Ile Pro Ile Val Tyr Tyr Gly Ser Glu Gln Ala Phe Ser Gly
305                 310                 315                 320

Ser Asn Asp Pro Ala Asn Arg Glu Asp Leu Trp Arg Ser Gly Tyr Asn
                325                 330                 335

Thr Glu Thr Asp Met Tyr Asn Ala Ile Ser Lys Leu Thr Phe Ala Lys
                340                 345                 350

His Thr Ala Gly Gly Leu Ala Asp Asn Asp His Lys His Leu Tyr Val
        355                 360                 365

Glu Pro Thr Ala Tyr Ala Trp Ser Arg Ala Gly Gly Lys Leu Val Ala
        370                 375                 380

Phe Thr Thr Asn Ser Gly Gly Ser Ser Ala Gln Phe Cys Phe Gly
385                 390                 395                 400

Thr Gln Val Pro Asn Gly Ser Trp Thr Asn Val Phe Asp Gly Gly Asn
                405                 410                 415

Gly Pro Thr Tyr Thr Ala Asp Gly Asn Gly Gln Leu Cys Leu Thr Thr
                420                 425                 430

Thr Asn Gly Glu Pro Ile Val Leu Leu Ser Ser
        435                 440

<210> SEQ ID NO 27
<211> LENGTH: 499
<212> TYPE: PRT
<213> ORGANISM: Aspergillus oryzae

<400> SEQUENCE: 27

Met Met Val Ala Trp Trp Ser Leu Phe Leu Tyr Gly Leu Gln Val Ala
1               5                   10                  15

Ala Pro Ala Leu Ala Ala Thr Pro Ala Asp Trp Arg Ser Gln Ser Ile
            20                  25                  30

Tyr Phe Leu Leu Thr Asp Arg Phe Ala Arg Thr Asp Gly Ser Thr Thr
        35                  40                  45

Ala Thr Cys Asn Thr Ala Asp Gln Lys Tyr Cys Gly Gly Thr Trp Gln
    50                  55                  60

Gly Ile Ile Asp Lys Leu Asp Tyr Ile Gln Gly Met Gly Phe Thr Ala
65                  70                  75                  80

Ile Trp Ile Thr Pro Val Thr Ala Gln Leu Pro Gln Thr Thr Ala Tyr
                85                  90                  95

Gly Asp Ala Tyr His Gly Tyr Trp Gln Gln Asp Ile Tyr Ser Leu Asn
            100                 105                 110

Glu Asn Tyr Gly Thr Ala Asp Asp Leu Lys Ala Leu Ser Ser Ala Leu
        115                 120                 125
```

-continued

```
His Glu Arg Gly Met Tyr Leu Met Val Asp Val Val Ala Asn His Met
                135                 140
130

Gly Tyr Asp Gly Ala Gly Ser Ser Val Asp Tyr Ser Val Phe Lys Pro
145                 150                 155                 160

Phe Ser Ser Gln Asp Tyr Phe His Pro Phe Cys Phe Ile Gln Asn Tyr
                165                 170                 175

Glu Asp Gln Thr Gln Val Glu Tyr Cys Trp Leu Gly Asp Asn Thr Val
                180                 185                 190

Ser Leu Leu Asp Leu Asp Thr Thr Lys Asp Val Val Lys Asn Glu Trp
            195                 200                 205

Tyr Asp Trp Val Gly Ser Leu Val Ser Asn Tyr Ser Ile Asp Gly Leu
210                 215                 220

Arg Ile Asp Thr Val Lys His Val Gln Lys Asp Phe Trp Pro Gly Tyr
225                 230                 235                 240

Asn Lys Ala Ala Gly Val Tyr Cys Ile Gly Glu Val Leu Asp Val Asp
                245                 250                 255

Pro Ala Tyr Thr Cys Pro Tyr Gln Asn Val Met Asp Gly Val Leu Asn
                260                 265                 270

Tyr Pro Ile Tyr Pro Leu Leu Asn Ala Phe Lys Ser Thr Ser Gly
                275                 280                 285

Ser Met Asp Asp Leu Tyr Asn Met Ile Asn Thr Val Lys Ser Asp Cys
290                 295                 300

Pro Asp Ser Thr Leu Leu Gly Thr Phe Val Glu Asn His Asp Asn Pro
305                 310                 315                 320

Arg Phe Ala Ser Tyr Thr Asn Asp Ile Ala Leu Ala Lys Asn Val Ala
                325                 330                 335

Ala Phe Ile Ile Leu Asn Asp Gly Ile Pro Ile Ile Tyr Ala Gly Gln
                340                 345                 350

Glu Gln His Tyr Ala Gly Gly Asn Asp Pro Ala Asn Arg Glu Ala Thr
            355                 360                 365

Trp Leu Ser Gly Tyr Pro Thr Asp Ser Glu Leu Tyr Lys Leu Ile Ala
370                 375                 380

Ser Ala Asn Ala Ile Arg Asn Tyr Ala Ile Ser Lys Asp Thr Gly Phe
385                 390                 395                 400

Val Thr Tyr Lys Asn Trp Pro Ile Tyr Lys Asp Asp Thr Thr Ile Ala
                405                 410                 415

Met Arg Lys Gly Thr Asp Gly Ser Gln Ile Val Thr Ile Leu Ser Asn
                420                 425                 430

Lys Gly Ala Ser Gly Asp Ser Tyr Thr Leu Ser Leu Ser Gly Ala Gly
            435                 440                 445

Tyr Thr Ala Gly Gln Gln Leu Thr Glu Val Ile Gly Cys Thr Thr Val
450                 455                 460

Thr Val Gly Ser Asp Gly Asn Val Pro Val Pro Met Ala Gly Gly Leu
465                 470                 475                 480

Pro Arg Val Leu Tyr Pro Thr Glu Lys Leu Ala Gly Ser Lys Ile Cys
                485                 490                 495

Ser Ser Ser
```

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Synthetic primer Tra2HisXhoI-r2

```
<400> SEQUENCE: 28
gctcgagtta gtggtggtgg tggtggtgtg aagacagcag caa                    43

<210> SEQ ID NO 29
<211> LENGTH: 462
<212> TYPE: PRT
<213> ORGANISM: Aspergillus nidulans

<400> SEQUENCE: 29

Met Lys Leu Ala Ser Thr Leu Ala Gly Leu Leu Pro Leu Ile Ser
1               5                   10                  15

Thr Val Ser Ala Ala Asp Val Asp Ala Trp Lys Ser Arg Asn Ile Tyr
                20                  25                  30

Phe Ala Leu Thr Asp Arg Val Ala Arg Gly Ser Asp Asp Thr Gly Gly
                35                  40                  45

Asp Ala Cys Asp Asp Leu Ser Thr Tyr Cys Gly Gly Thr Phe Lys Gly
                50                  55                  60

Leu Glu Gly Lys Leu Asp Tyr Ile Lys Gly Met Gly Phe Asp Ala Ile
65                  70                  75                  80

Trp Ile Thr Pro Val Val Ala Asn His Asp Gly Gly Tyr His Gly Tyr
                85                  90                  95

Trp Ala Lys Asp Leu Tyr Ser Ile Asn Glu Asn Tyr Gly Thr Ala Asp
                100                 105                 110

Asp Leu Lys Ser Leu Val Ser Ala Ala His Glu Lys Gly Ile Tyr Ile
                115                 120                 125

Met Ala Asp Val Val Ala Asn His Met Gly Ser Pro Ile Ser Asp Asn
                130                 135                 140

Gln Pro Glu Ser Leu Ser Gln Glu Ser Ala Tyr His Ser Ala Cys Thr
145                 150                 155                 160

Ile Asp Tyr Ser Ser Gln Glu Ser Ile Glu Thr Cys Arg Ile Ala Asp
                165                 170                 175

Asp Leu Pro Asp Val Asn Thr Glu Ser Glu Ile Arg Thr Leu Phe
                180                 185                 190

Lys Glu Trp Ile Thr Trp Leu Val Lys Glu Tyr Glu Phe Asp Gly Leu
                195                 200                 205

Arg Ile Asp Thr Val Lys His Val Glu Lys Asp Phe Trp Ser Asp Phe
                210                 215                 220

Ser Ser Ala Ala Gly Val Tyr Thr Ile Gly Glu Val Phe Asp Gly Asp
225                 230                 235                 240

Pro Asp Tyr Leu Ala Gly Tyr Ala Asn Thr Met Asp Gly Leu Leu Asn
                245                 250                 255

Tyr Ala Val Tyr Tyr Pro Val Asn Asn Phe Tyr Gln Gln Ala Gly Ser
                260                 265                 270

Ala Gln Asp Ile Val Asp Met His Asp Lys Ile Asp Ser Ser Phe Pro
                275                 280                 285

Asp Pro Ser Ala Leu Gly Thr Phe Ile Asp Asn His Asp Asn Ala Arg
                290                 295                 300

Trp Leu Ser Asn Lys Asp Asp Lys Ser Leu Leu Lys Asn Ala Leu Ala
305                 310                 315                 320

Tyr Val Ile Leu Ala Arg Gly Ile Pro Ile Val Tyr Tyr Gly Thr Glu
                325                 330                 335

Gln Gly Tyr Ala Gly Gly Asn Asp Pro Glu Asn Arg Glu Asp Leu Trp
                340                 345                 350

Arg Ser Asn Phe Asp Thr Asp Ala Asp Leu Tyr Lys Ala Ile Ser Leu
                355                 360                 365
```

-continued

Leu Ser Ala Ala Arg Ser Ala Ala Gly Gly Leu Gly Asp Asn Asp His
    370                 375                 380

Val His Leu His Val Ala Glu Ser Ala Tyr Ala Trp Ser Arg Ala Glu
385                 390                 395                 400

Gly Lys Leu Val Val Thr Ser Asn Ser Gly Ser Gly Ser Glu Asn
            405                 410                 415

Glu Ile Cys Phe Asp Ser Lys Thr Pro Asn Gly Ser Trp Glu Asn Ile
            420                 425                 430

Phe Gly Glu Gly Thr Ile Ser Ala Asp Asp Ser Gly Gln Ile Cys Val
            435                 440                 445

Ser Ile Thr Asn Gly Glu Pro Ala Val Leu Val Ala Gln Ser
    450                 455                 460

<210> SEQ ID NO 30
<211> LENGTH: 485
<212> TYPE: PRT
<213> ORGANISM: Gibberella zeae

<400> SEQUENCE: 30

Met Lys Leu Leu Gln Leu Ala Ala Leu Val Ala Ser Ile Ser Pro Phe
1               5                   10                  15

Ala Ser Ala Ala Asp Ala Asn Ala Trp Lys Ser Arg Asn Ile Tyr Phe
            20                  25                  30

Ala Leu Thr Asp Arg Val Ala Arg Ser Asp Ser Asp Ser Gly Gly Asn
            35                  40                  45

Ala Cys Ser Asn Leu Gly Asn Tyr Cys Gly Gly Thr Phe Lys Gly Leu
    50                  55                  60

Glu Ala Lys Leu Asp Tyr Ile Lys Gly Met Gly Phe Asp Ala Ile Trp
65                  70                  75                  80

Ile Thr Pro Val Val Glu Asn Thr Asp Gly Gly Tyr His Gly Tyr Trp
                85                  90                  95

Ala Lys Asp Leu Leu Pro Asp Leu Asn Thr Gly Ser Glu Thr Val Lys
            100                 105                 110

Lys Val Leu Asn Asp Trp Ile Ser Trp Leu Val Thr Glu Tyr Ser Phe
        115                 120                 125

Asp Gly Ile Arg Ile Asp Thr Val Lys His Val Glu Lys Ser Phe Trp
    130                 135                 140

Pro Asp Phe Gln Lys Ala Ala Gly Val Tyr Ala Ile Gly Glu Val Trp
145                 150                 155                 160

Asp Gly Ser Pro Asp Tyr Leu Ala Gly Tyr Ser Lys Val Ile Gln Asp
                165                 170                 175

His Arg Pro Glu Pro Leu Asn Gln Gln Ser Ser Tyr His Ser Pro Cys
            180                 185                 190

Ala Ile Asp Tyr Asn Asn Gln Asn Ser Ile Glu Gln Cys Glu Ile Ala
        195                 200                 205

Asp Tyr Glu Val Asn Ala Lys Tyr Gly Thr Lys Asp Asp Leu Lys Ser
    210                 215                 220

Leu Val Lys Thr Ala His Ser Lys Asn Ile Tyr Val Met Ala Asp Val
225                 230                 235                 240

Val Ala Asn His Met Gly Lys Gly Met Pro Gly Leu Leu Asn Tyr Ala
                245                 250                 255

Ile Tyr Tyr Pro Met Asn Arg Phe Tyr Gln Gln Lys Gly Asp Pro Ser
            260                 265                 270

Ala Val Val Asp Met Tyr Asn Glu Ile Ser Gln Lys Phe Asp Asp Pro
        275                 280                 285

```
Thr Val Leu Gly Thr Phe Ile Asp Asn His Asp Asn Pro Arg Trp Leu
        290                 295                 300
Ser Gln Lys Asn Asp Lys Ala Leu Leu Lys Asn Ala Leu Ala Tyr Val
305                 310                 315                 320
Ile Leu Ser Arg Gly Ile Pro Ile Val Tyr Tyr Gly Thr Glu Gln Gly
                325                 330                 335
Tyr Ala Gly Gly Asn Asp Pro Ala Asn Arg Glu Asp Leu Trp Arg Ser
            340                 345                 350
Ser Phe Lys Thr Asp Ser Asp Leu Tyr Gln Thr Ile Ser Lys Leu Gly
        355                 360                 365
Lys Ala Arg Ser Ala Val Gly Gly Leu Ala Gly Asn Asp Gln Lys Phe
    370                 375                 380
Leu Lys Ser Asn Asp Ser Ala Leu Ile Trp Ser Arg Ala Asn Val Lys
385                 390                 395                 400
Ser Asp Gly Ser Gly Gln Leu Cys Val Ser Tyr Thr Asn Gly Glu Pro
                405                 410                 415
Glu Val Leu Val Ala Ala Asn Asn Asp Leu Ile Val Val Thr Met Asn
            420                 425                 430
Arg Gly Gln Gly Phe Ser Gly Gln Tyr Cys Phe Asn Thr Gly Ala Asn
        435                 440                 445
Asn Lys Thr Trp Glu Arg Val Leu Gly Gln Gly Thr Val Lys Ser Asp
    450                 455                 460
Gly Ser Gly Gln Leu Cys Val Ser Tyr Thr Asn Gly Gly Pro Glu Val
465                 470                 475                 480
Leu Val Ala Ala Asn
                485

<210> SEQ ID NO 31
<211> LENGTH: 600
<212> TYPE: PRT
<213> ORGANISM: Magnaporthe grisea

<400> SEQUENCE: 31

Met Phe Phe Phe Lys Val Leu Val Ala Phe Leu Leu Gln Ile Val Thr
1               5                   10                  15
Val Tyr Ala Ala Asp Thr Ala Ala Trp Lys Ser Arg Ser Ile Tyr Phe
            20                  25                  30
Ala Leu Thr Asp Arg Val Ala Arg Gly Ser Asn Asp Thr Gly Gly Ala
        35                  40                  45
Ser Cys Gly Asn Leu Ser Lys Tyr Cys Gly Gly Thr Phe Lys Gly Leu
    50                  55                  60
Glu Ser Lys Leu Asp Tyr Ile Lys Asn Leu Gly Phe Asp Ser Ile Trp
65                  70                  75                  80
Ile Asn Pro Val Val Ser Asn Lys Ala Asp Gly Tyr His Gly Tyr Trp
                85                  90                  95
Ala Gln Asp Leu Tyr Ala Ile Asn Ser Asn Tyr Gly Ser Ala Ala Asp
            100                 105                 110
Leu Lys Ser Leu Val Asn Thr Ala His Ser Lys Gly Ile Tyr Val Met
        115                 120                 125
Val Asp Val Val Ala Asn His Met Gly Pro Gly Ser Ile Ser Asp Asn
    130                 135                 140
Arg Pro Ala Pro Leu Asn Gln Asn Ser Ser Tyr His Ser Gln Cys Thr
145                 150                 155                 160
Ile Asp Asn Ser Asn Gln Ser Ser Val Glu Asn Cys Trp Val Ala Asn
                165                 170                 175
```

```
Leu Pro Asp Ile Asn Thr Gln Ser Ser Gly Ile Arg Gln Leu Leu Asn
                180                 185                 190

Thr Trp Val Ser Trp Leu Val Lys Glu Tyr Ser Phe Asp Gly Val Arg
            195                 200                 205

Ile Asp Thr Val Lys His Val Glu Lys Ser Phe Trp Pro Gly Phe Val
        210                 215                 220

Lys Ser Ile Gly Ala Tyr Ala Ile Gly Glu Val Phe Asp Gly Asn Pro
225                 230                 235                 240

Ser Phe Met Ala Gly Tyr Ala Asn Leu Met Pro Gly Leu Leu Asn Tyr
                245                 250                 255

Ala Val Tyr Tyr Pro Met Asn Arg Phe Tyr Gln Gln Gly Asn Ser Pro
            260                 265                 270

Gln Glu Leu Val Asn Met Ile Asp Asn Ile Thr Ala Ser Phe Pro Asp
        275                 280                 285

Pro Ala Ala Leu Gly Thr Phe Leu Asp Asn His Asp Asn Pro Arg Trp
290                 295                 300

Leu Asn Gln Thr Asn Asp Gln Thr Leu Leu Gln Asn Ala Leu Ala Phe
305                 310                 315                 320

Val Phe Leu Ser Arg Gly Ile Pro Ile Leu Tyr Tyr Gly Thr Glu Gln
                325                 330                 335

Gly Leu Val Gly Gly Asp Asp Pro Ala Asn Arg Glu Asp Leu Trp Arg
            340                 345                 350

Ser Gly Tyr Lys Thr Asp Thr Thr Leu His Gly Ala Val Ala Lys Leu
        355                 360                 365

Asn Ala Ala Arg Lys Ala Ala Gly Gly Leu Asp Gly Asn Asp His Thr
370                 375                 380

His Leu Tyr Val Thr Asn Asp Thr Tyr Ala Trp Ser Arg Ala Gly Ala
385                 390                 395                 400

Asp Leu Val Val Leu Thr Thr Asn Ala Gly Arg Cys Ser His Ala Gln
                405                 410                 415

His Cys Phe Asn Thr Thr Arg Ala Asn Gly Arg Trp Ala Asp Val Tyr
            420                 425                 430

Gly Ser Gly Ala Tyr Val Phe Ser Asp Lys Thr Gly Arg Ala Cys Val
        435                 440                 445

Lys Leu Ala Asn Gly Gln Pro Val Val Leu Ala Leu Ala Asn Ser
450                 455                 460

Thr Thr Gly Asp Gly Lys Pro Pro Thr Leu Pro Ala Pro Ile Thr Trp
465                 470                 475                 480

Tyr Asn Ser Thr Ser Pro Pro Asp Asp Ser Ala Asn Gly Ser Asn Val
                485                 490                 495

Cys Pro Pro Ala Val Ala Val Ser Phe Thr Val Arg Val Ala Thr Ala
            500                 505                 510

Pro Gly Asp Thr Ile Lys Met Val Gly Asn Thr Ala Gln Leu Gly Ser
        515                 520                 525

Trp Asp Ala Ala Lys Ala Pro Ser Leu Ser Ala Ser Gly Tyr Asn Ser
530                 535                 540

Thr Asn Met Ala Trp Ser Ile Thr Leu Pro Met Ala Pro Gly Arg Thr
545                 550                 555                 560

Val Gln Tyr Lys Phe Val Lys Val Ser Arg Ser Gly Gly Thr Thr Trp
                565                 570                 575

Glu Ser Asp Pro Asn Arg Phe Tyr Thr Pro Pro Val Ser Gln Ala Thr
            580                 585                 590

Ala Asp Val Ser Asn Ile Trp Arg
```

<210> SEQ ID NO 32
<211> LENGTH: 686
<212> TYPE: PRT
<213> ORGANISM: Magnaporthe grisea

<400> SEQUENCE: 32

Met Ala Asn Lys Ile Leu Val Ala Tyr Ile Phe Ala Asp Phe Leu Phe
1               5                   10                  15

Val Leu Met Gly Ala Leu Met Leu Gly Phe Ser Ile Val Val Gly Asn
            20                  25                  30

Val Arg Asp Glu Val Pro Thr Glu Gly Asn Gln Ala Ala Arg Asn Leu
        35                  40                  45

Leu Tyr Gln Lys Phe Pro Leu Thr Ala Gly Ile Val Asn Ala Ile Phe
    50                  55                  60

Ile Phe Ile Thr Phe Leu Leu Thr Ile Pro Ala Leu Ser Thr Pro Ala
65                  70                  75                  80

Arg Gly Trp Leu Lys Met Ser Gly Tyr Leu Val Val Asn Ala Leu
                85                  90                  95

Phe Ser Leu Val Ile Gly Leu Phe Leu Trp Ile Met Thr Leu Lys Thr
            100                 105                 110

Arg Asp Asp Leu Phe Pro Ile Trp Val Gln Gln Thr Pro Gln Val Gln
        115                 120                 125

Ser Leu Met Glu Val Ser Phe Lys Cys Cys Gly Tyr Tyr Asn Ser Thr
    130                 135                 140

Ala Pro Ala Phe Val Thr Asn Gln Val Cys Pro Ser Pro Ala Ala Ser
145                 150                 155                 160

Ala Leu Met Arg Gly Cys Ala Thr Pro Ile Thr Ser Phe Ala Asn Val
                165                 170                 175

Phe Val Asp Asn Ile Phe Thr Gly Val Phe Gly Met Cys Gly Ile Asp
            180                 185                 190

Gly Leu Leu Val Ile Ala Thr Ala Cys Leu Leu Lys Asp Arg Lys Glu
        195                 200                 205

Gln Glu Arg Phe Arg His Ile Asp Gln Lys Thr Gly Pro Met Ser Thr
    210                 215                 220

Leu Pro Gly Gln Thr Ser Val Arg Gln Ala Asp Arg Ile Ala Arg
225                 230                 235                 240

Asn Glu Ser Asp Ser Gly Gly Asn Ser Cys Ser Asp Leu Gly Gln Tyr
                245                 250                 255

Cys Gly Gly Thr Phe Lys Gly Leu Gln Ser Lys Leu Asp Tyr Ile Arg
            260                 265                 270

Gly Met Gly Phe Asp Ala Ile Trp Ile Ser Pro Val Val Glu Asn His
        275                 280                 285

Lys Gly Gly Tyr His Gly Tyr Trp Ala Lys Asp Leu Tyr Ala Ile Asn
    290                 295                 300

Ser Lys Tyr Gly Thr Ala Asp Asp Leu Lys Ser Leu Ile Lys Ala Ala
305                 310                 315                 320

His Asp Lys Gly Phe Leu Met Val Asp Val Ala Asn His Met
                325                 330                 335

Gly Asn Gly Pro Ile Ser Glu Asn Lys Pro Ala Pro Leu Asn Gln Glu
            340                 345                 350

Ser Ser Tyr His Pro Glu Cys Lys Ile Asp Tyr Ser Asn Gln Gln Ser
        355                 360                 365

Val Glu Arg Cys Arg Leu Gly Asn Leu Pro Asp Leu Asn Thr Glu Asp

```
                370              375              380
Pro Lys Ile Arg Thr Leu Leu Thr Asp Trp Ile Lys Trp Ile Val Ser
385              390              395              400

Glu Phe Lys Val Asp Gly Leu Arg Ile Asp Thr Val Lys His Val Glu
                405              410              415

Lys Gly Phe Trp Pro Gly Phe Ala Trp Ala Ser Gly Val Tyr Thr Leu
                420              425              430

Gly Glu Val Tyr Ser Glu Asp Val Asp Tyr Leu Ala Gly Tyr Asp Lys
                435              440              445

Thr Met Gly Gly Phe Phe Asn Phe Pro Val Tyr Lys Ser Leu Gly Arg
450              455              460

Tyr Leu Gln Gln Gly Gln Ser Pro Gln Gly Leu Val Asp Asn His Asp
465              470              475              480

Lys Ile Thr Arg Lys Phe Ser Asp Pro Thr Thr Leu Ala Asn Phe Leu
                485              490              495

Asp Ser His Asp Asp Pro Arg Trp Leu Ser Lys Asn Arg Asp Ala Ala
                500              505              510

Leu Leu Lys Asn Ala Leu Ala Tyr Val Leu Leu Ala Arg Gly Ile Pro
                515              520              525

Val Val Tyr Tyr Gly Thr Glu Gln Gly Phe Ser Gly Gly Ala Asp Pro
530              535              540

Trp Asn Arg Glu Asp Leu Trp Arg Ala Arg Tyr Arg Thr Asp Gly Asp
545              550              555              560

Leu Tyr Arg Ala Ile Ser Arg Leu Ser Gly Val Arg Ala Gly Ala Gly
                565              570              575

Gly Leu Pro Ala Asp Asp Gln Ile His Leu Leu Val Asn Lys Asn Ser
                580              585              590

Tyr Ala Phe Ser Arg Asp Gly Tyr Thr Ser Asp Glu Ser Gly Lys Val
                595              600              605

Cys Val Gln Val Lys Asn Gly Glu Pro Val Val Leu Val Arg Lys Lys
                610              615              620

Gly Gly Val Val Leu Thr Thr Asn Arg Gly Ser Gly Phe Asn Gly
625              630              635              640

Gln Glu Cys Phe Asp Thr Arg Gly Val Thr Ala Thr Trp Glu Asp Lys
                645              650              655

Phe Gly Ser Gly Thr Tyr Thr Ser Asp Glu Ser Gly Lys Val Cys Val
                660              665              670

Gln Val Lys Asn Gly Glu Pro Val Val Lys Val Arg Lys Lys
                675              680              685

<210> SEQ ID NO 33
<211> LENGTH: 550
<212> TYPE: DNA
<213> ORGANISM: Trichoderma sp.
<220> FEATURE:
<223> OTHER INFORMATION: Strain IAM5141

<400> SEQUENCE: 33
tggagagcaa gctggactac atcaagggca tgggatttga tgccatctgg atcaaccccg      60
tcgtaaccag tgagttgccc atctatcccc atcctcttga ttggtggcta acatctcttg     120
aaagacagtg atttcggctt ccatggctac tgggcactgg atctaaacac tatcaattct     180
cactatggca ctgcggatga tttaaagagt ctcgttgatg ctgcacatgg caagtatat      240 tcacaccatt ctcccaactg ctgagtgtca gtgctagaaa taaccaaaaa cagggcttct     300
acatgatggt cgacgttgta gccaaccaca tgggaaacgc aaacatcaca gacgactccc     360
```

-continued

```
cctcccctct gaaccaacaa tcctcatacc acacaaaatg tgacattgac ttcaacaacc    420
agaccagcgt cgaaaactgt tggcttgctg gcctcccaga cgttgacacc caggaccta    480 ccatcaggag cctctaccag gactgggtgt ccaacctggt atctacatac ggcttcgacg    540
gcgtccgcat                                                           550
```

POLYNUCLEOTIDE ENCODING A POLYPEPTIDE HAVING GLYCOSYLATION ACTIVITY ON A FLAVONOID

TECHNICAL FIELD

The present invention relates to novel glycosyltransferases which allow glycosylation of flavonoid compounds, and polynucleotides encoding the same. Glycosides of flavonoid compounds obtained by the present invention can be used for food, pharmaceutical and cosmetic purposes.

BACKGROUND ART

Proanthocyanidin (grape seed extract) has been studied for its usefulness as a therapeutic agent for blood vessels, and one of the reasons for recent progress in these studies is that the target substance can serve as a marker for tracing in vivo absorption and metabolism because it is stable against heat and acids, highly soluble in water and highly absorbable in the body. In contrast, polyphenol compounds such as catechin are often difficult to dissolve in water, and also involve a problem in that they are less absorbable in the body.

Attempts have been made to develop a technique for glycosylation of catechin and other compounds, with the aim of improving their solubility in water and increasing their stability.

By way of example, Patent Document 1 discloses α-glucosidase with a molecular weight of about 57,000, which was collected from a culture solution of *Xanthomonas campestris* WU-9701. This enzyme uses maltose or the like as a donor (does not use maltotriose, cyclodextrin or starch as a donor) and transfers glucose to a specific acceptor to synthesize a glycoside. In this document, compounds listed as acceptors are those having an alcoholic hydroxyl group (e.g., menthol, ethanol, 1-propanol, 1-butanol, 2-butanol, isobutyl alcohol, 1-amyl alcohol, 2-amyl alcohol, 5-nonyl alcohol), as well as those having a phenolic hydroxyl group (e.g., capsaicin, dihydrocapsaicin, nonylic acid vanillylamide, catechin, epicatechin, vanillin, hydroquinone, catechol, resorcinol, 3,4-dimethoxyphenol). Moreover, glycosides whose production was actually confirmed are monoglucosides only.

Patent Document 2 discloses a method in which a mixture of a catechin compound and glucose-1-phosphate or sucrose is treated with sucrose phosphorylase to prepare a glycoside of the catechin compound. The sources of sucrose phosphorylase listed therein are *Leuconostoc mesenteroides*, *Pseudomonas saccharophila*, *Pseudomonas putrefaciens*, *Clostridium pasteurianum*, *Acetobacter xylinum*, and *Pullularia pullulans*. Likewise, catechin compounds listed as acceptors are (+)-catechin, (−)-epicatechin, (−)-epicatechin 3-O-gallate, (−)-epigallocatechin and (−)-epigallocatechin 3-O-gallate, but it is only (+)-catechin that was actually used as an acceptor to prepare (+)-catechin 3'-O-α-D-glucopyranoside in the Example section.

Patent Document 3 discloses epigallocatechin 3-O-gallate derivatives, in which a glucose residue or a maltooligosaccharide residue with a polymerization degree of 2 to 8 is attached to at least one of the 5-, 7-, 3'-, 4'-, 5'-, 3"-, 4"- and 5"-positions. As in the case of Patent Document 2, the Example section of Patent Document 3 actually discloses only a case where a mixture of (−)-epigallocatechin gallate and glucose-1-phosphate or sucrose was treated with sucrose phosphorylase to prepare 4'-O-α-D-glucopyranosyl(−)-epigallocatechin gallate and 4',4"-O-α-D-di-glucopyranosyl(−)-epigallocatechin gallate.

Patent Document 4 discloses tea extracts or tea beverages whose astringent taste is reduced by glycosylation of polyphenols contained therein. To reduce the astringent taste of tea extracts or tea beverages, this document describes detailed procedures in which tea extracts or tea beverages are supplemented with dextrin, cyclodextrin, starch or a mixture thereof, and then treated with cyclomaltodextrin glucanotransferase. In the Example section, it is shown that a green tea extract and α-cyclodextrin were treated with cyclomaltodextrin glucanotransferase derived from *Bacillus stearothermophilus* to give a reaction product with reduced astringent taste, which in turn indicates that polyphenols such as epigallocatechin 3-O-gallate and epicatechin were glycosylated. However, this document fails to show the detailed structure of the reaction product.

Patent Document 5 discloses glycosides of catechin compounds in which glycosylation occurs at the 3'-position, at the 3'- and 5-positions, or at the 3'- and 7-positions. For this purpose, this document describes detailed procedures in which a catechin compound and dextrin, cyclodextrin, starch or a mixture thereof are treated with cyclomaltodextrin glucanotransferase derived from *Bacillus stearothermophilus*, as in the case of Patent Document 4. Further, in the examples using dextrin as a glycosyl donor in the above procedures, some of the resulting glycosides of (−)-epigallocatechin, (−)-epigallocatechin 3-O-gallate and (−)-epicatechin 3-O-gallate are considered to have 6 to 8 glucose residues on average per molecule of each polyphenol, as determined from their molar absorption coefficients. Moreover, it is confirmed that upon treatment with glucoamylase derived from *Rhizopus niveus*, the glycosides obtained by the above procedures generated 3',7-di-O-α-α-glucopyranosyl(−)-epigallocatechin, 3',5-di-O-α-D-glucopyranosyl(−)-epigallocatechin, 3'-O-α-D-glucopyranosyl(−)-epigallocatechin, 3',7-di-O-α-D-glucopyranosyl(−)-epigallocatechin 3-O-gallate, 3'-O-α-D-glucopyranosyl(−)-epigallocatechin 3-O-gallate, 3'-O-α-D-glucopyranosyl(−)-gallocatechin and 3'-O-α-D-glucopyranosyl(−)-epicatechin 3-O-gallate.

As to effects provided by catechin glycosides, Non-patent Document 1 describes reduced astringent taste, increased water-solubility, improved stability and inhibited tyrosinase, while Non-patent Document 2 describes suppressed mutagenicity.

Patent Document 1: JP 2001-46096 A
Patent Document 2: JP 05-176786 A (Japanese Patent No. 3024848)
Patent Document 3: JP 07-10897 A (Japanese Patent No. 3071610)
Patent Document 4: JP 08-298930 A (Japanese Patent No. 3579496)
Patent Document 5: JP 09-3089 A (Japanese Patent No. 3712285)
Non-patent Document 1: Biosci. Biotech. Biochem., 57 (10), 1666-1669 (1993)
Non-patent Document 2: Biosci. Biotech. Biochem., 57 (10), 1290-1293 (1993)

DISCLOSURE OF THE INVENTION

Problems to be Solved by the Invention

These glycosylation techniques cannot be regarded as sufficient in terms of properties of the enzymes used therein, including glycosyl donor specificity, specificity to compounds which can be glycosylated, glycosylation efficiency, etc. Thus, there has been a demand for the development of glycosyltransferases with more excellent properties.

Means for Solving the Problems

The inventors of the present invention have made extensive and intensive efforts to develop a glycosylation technique for flavonoid including catechin. As a result, the inventors have found a novel glycosyltransferase from the culture supernatant of *Trichoderma viride* and have cloned a gene thereof, thereby completing the present invention.

[Glycosyltransferase Genes and Others]

The present invention provides a polynucleotide or a homolog thereof, which encodes a glycosyltransferase protein produced by ascomycetous filamentous fungi (preferably species belonging to the genus *Trichoderma*, more preferably *Trichoderma viride*), i.e., a polynucleotide comprising any one of (A) to (K) shown below (preferably a polynucleotide consisting of any one of (A) to (K) shown below):

(A) a polynucleotide which consists of all or part of the nucleotide sequence shown in SEQ ID NO: 6 (e.g., all or part of nucleotides 423-1928, a region corresponding to the nucleotide sequence of SEQ ID NO: 9);

(B) a polynucleotide which is hybridizable under stringent conditions with a polynucleotide consisting of a nucleotide sequence complementary to the nucleotide sequence of the polynucleotide shown in (A) and which encodes a protein having glycosylation activity on a flavonoid compound;

(C) a polynucleotide which consists of a nucleotide sequence comprising substitution, deletion, insertion and/or addition of one or several nucleotides in the nucleotide sequence of the polynucleotide shown in (A) and which encodes a protein having glycosylation activity on a flavonoid compound;

(D) a polynucleotide which shares an identity of at least 60% or more with the nucleotide sequence of the polynucleotide shown in (A) and which encodes a protein having glycosylation activity on a flavonoid compound;

(E) a polynucleotide which consists of the nucleotide sequence shown in SEQ ID NO: 9;

(F) a polynucleotide which is hybridizable under stringent conditions with a polynucleotide consisting of a nucleotide sequence complementary to the nucleotide sequence of the polynucleotide shown in (E) and which encodes a protein having glycosylation activity on a flavonoid compound;

(G) a polynucleotide which consists of a nucleotide sequence comprising substitution, deletion, insertion and/or addition of one or several nucleotides in the nucleotide sequence of the polynucleotide shown in (E) and which encodes a protein having glycosylation activity on a flavonoid compound;

(H) a polynucleotide which shares an identity of at least 60% or more with the nucleotide sequence of the polynucleotide shown in (E) and which encodes a protein having glycosylation activity on a flavonoid compound;

(I) a polynucleotide which encodes a protein consisting of the amino acid sequence shown in SEQ ID NO: 10;

(J) a polynucleotide which encodes a protein consisting of an amino acid sequence comprising substitution, deletion, insertion and/or addition of one or several amino acids in the amino acid sequence shown in SEQ ID NO: 10 and having glycosylation activity on a flavonoid compound; and (K) a polynucleotide which encodes a protein consisting of an amino acid sequence sharing an identity of at least 60% or more with the amino acid sequence shown in SEQ ID NO: 10 and having glycosylation activity on a flavonoid compound.

SEQ ID NO: 6 shows the nucleotide sequence of genomic DNA for glycosyltransferase TRa2 obtained from *T. viride* strain IAM5141, while SEQ ID NOs: 9 and 10 show the cDNA and deduced amino acid sequences thereof, respectively.

When the deduced amino acid sequence of TRa2 is analyzed by Signal P, a sequence covering amino acids 1-20 of SEQ ID NO: 10 is predicted as a secretion signal. Thus, a mature protein essential for serving as a glycosyltransferase lies in the sequence downstream of amino acid 21 in SEQ ID NO: 10; it would be suitable to remove the signal sequence if this enzyme is expressed in a heterologous expression system such as *E. coli*. Polynucleotides encoding such a mature protein also fall within the scope of the present invention.

Thus, the present invention also provides a polynucleotide comprising any one of (L) to (R) shown below (preferably a polynucleotide consisting of any one of (L) to (R) shown below):

(L) a polynucleotide which consists of the nucleotide sequence shown in SEQ ID NO: 25;

(M) a polynucleotide which is hybridizable under stringent conditions with a polynucleotide consisting of a nucleotide sequence complementary to the nucleotide sequence shown in SEQ ID NO: 25 and which encodes a protein having glycosylation activity on a flavonoid compound;

(N) a polynucleotide which consists of a nucleotide sequence comprising substitution, deletion, insertion and/or addition of one or several nucleotides in the nucleotide sequence of the polynucleotide shown in SEQ ID NO: 25 and which encodes a protein having glycosylation activity on a flavonoid compound;

(O) a polynucleotide which shares an identity of at least 60% or more with the nucleotide sequence shown in SEQ ID NO: 25 and which encodes a protein having glycosylation activity on a flavonoid compound;

(P) a polynucleotide which encodes a protein consisting of the amino acid sequence shown in SEQ ID NO: 26;

(Q) a polynucleotide which encodes a protein consisting of an amino acid sequence comprising substitution, deletion, insertion and/or addition of one or several amino acids in the amino acid sequence shown in SEQ ID NO: 26 and having glycosylation activity on a flavonoid compound; and (R) a polynucleotide which encodes a protein consisting of an amino acid sequence sharing an identity of at least 60% or more with the amino acid sequence shown in SEQ ID NO: 26 and having glycosylation activity on a flavonoid compound.

SEQ ID NO: 25 shows the nucleotide sequence of cDNA encoding TRa2 as a mature protein, i.e., a nucleotide sequence covering nucleotides 61-1389 of SEQ ID NO: 9. Likewise, SEQ ID NO: 26 shows the amino acid sequence of TRa2 as a mature protein, i.e., an amino acid sequence covering amino acids 21-463 of SEQ ID NO: 10.

The present invention also provides a polynucleotide which is derived from the genus *Trichoderma* (preferably *Trichoderma viride, Trichoderma reesei, Trichoderma saturnisporum, Trichoderma ghanense, Trichoderma koningii, Trichoderma hamatum, Trichoderma harzianum* or *Trichoderma polysporum*), comprises any one of the nucleotide sequences shown in SEQ ID NOs: 11 to 24, and encodes a protein having glycosylation activity on a flavonoid compound. A preferred example of such a polynucleotide is a polynucleotide which comprises any one of the nucleotide sequences shown in SEQ ID NOs: 11 to 24, shares high identity with the nucleotide sequence shown in SEQ ID NO: 6, 9 or 25, and encodes a protein having glycosylation activity on a flavonoid compound.

As used herein, the term "glycosylation activity" is intended to mean having the ability to transfer a sugar residue to a flavonoid compound. To confirm whether a protein has the ability to transfer a sugar residue to a flavonoid compound, unless otherwise specified, a mixture of flavonoid (e.g., catechin) and an appropriate glycosyl donor (e.g., dextrin) may be contacted with the target enzyme and reacted for a sufficient period of time, followed by analysis of the reaction solution through high performance liquid chromatography (HPLC) or other techniques, for example as shown in the Example section described later.

A protein encoded by the polynucleotide of the present invention may have not only glycosylation activity, but also an additional activity, such as dextrinase activity. As used herein, the term "dextrinase" is intended to mean an enzyme capable of hydrolyzing carbohydrates containing α-glucoside linkages (e.g., starch, dextrin), unless otherwise specified. Dextrinase is a kind of amylase. To determine whether a target has dextrinase activity, a commercially available dextrin (e.g., starch hydrolyzed with an acid, heat or an enzyme to have an average molecular weight of about 3,500) may be treated with the target under appropriate conditions to examine whether the dextrin is hydrolyzed. Those skilled in the art would design appropriate conditions for reaction with a target and procedures for determining whether dextrin is hydrolyzed.

(Flavonoid Compounds)

As used herein, the term "flavonoid compound" is intended to include both flavonoid and esculetin, unless otherwise specified.

As used herein, the term "flavonoid" is intended to mean a catechin compound (flavanol), flavanone, flavone, flavonol, flavanonol, isoflavone, anthocyan or chalcone, as well as a methylated derivative thereof, unless otherwise specified. Flavonoid includes naringenin, quercetin, daidzein, genistein and kaempferol. Flavonoid available for use in the present invention may be of natural or synthetic origin.

As used herein, the term "catechin compound" is used in a broad sense to mean a polyoxy derivative of 3-oxyflavan, unless otherwise specified. This includes catechin, gallocatechin and 3-galloyl derivatives thereof, as well as optical isomers ((+)-, (−)-, (+)-epi- and (−)-epi-isomers) and racemates thereof. Specific examples include catechin, gallocatechin (GC), catechin gallate (catechin-3-O-gallate; CG), gallocatechin gallate (gallocatechin-3-O-gallate; GCG), epicatechin (EC), epigallocatechin (EGC), epicatechin gallate (epicatechin-3-O-gallate; ECG) and epigallocatechin gallate (epigallocatechin-3-O-gallate; EGCG), as well as optical isomers thereof. Methylated derivatives of catechin compounds refer to derivatives of the above catechin compounds, in which H in at least one OH group is replaced by methyl. Examples of methylated derivatives of catechin compounds include those having methyl in place of H in the OH group located at any of the 3'-, 4'-, 3"- and 4"-positions of epicatechin, epigallocatechin, epicatechin gallate or epigallocatechin gallate. Catechin compounds and their methylated derivatives available for use in the present invention may be of natural or synthetic origin. Examples of natural origin include tea extracts, concentrated and purified products thereof (e.g., green tea extracts such as Teavigo (DSM Nutrition Japan), Polyphenon (Mitsui Norin Co., Ltd., Japan) and Sunphenon (Taiyo Kagaku Co., Ltd., Japan)), as well as extracts of a tea cultivar "Benifuki."

In the present invention, flavonoid compounds may be used either alone or in combination.

(Glycosyl Donors)

As used herein, the term "glycosyl donor" is intended to mean a carbohydrate which can serve as a substrate for an enzyme in the method of the present invention and can be hydrolyzed to supply a sugar residue to a flavonoid compound, unless otherwise specified. Glycosyl donors available for use in the present invention are carbohydrates containing a maltotriose residue, including maltotriose, maltotetraose, maltopentaose, maltohexaose, maltoheptaose, dextrin, γ-cyclodextrin and soluble starch. As used herein, the term "dextrin" is intended to mean a hydrolysate of starch, unless otherwise specified, while the term "soluble starch" is intended to mean a hydrolysate of starch, which is soluble in hot water, unless otherwise specified. Hydrolysis may be accomplished by using any means such as an acid, heat or an enzyme. In the present invention, it is possible to use a hydrolysate having an average molecular weight of about 3,500 as an example of dextrin and a hydrolysate having an average molecular weight of about 1,000,000 as an example of soluble starch.

As used herein, the term "stringent conditions" refers to conditions of 6 M urea, 0.4% SDS and 0.5×SSC, or hybridization conditions equivalent thereto, unless otherwise specified. If necessary, more stringent conditions (e.g., 6 M urea, 0.4% SDS and 0.1×SSC) or hybridization conditions equivalent thereto may be applied in the present invention. Under each of these conditions, the temperature may be set to about 40° C. or higher. When more stringent conditions are required, the temperature may be set to a higher value, for example about 50° C. and more particularly about 65° C.

Moreover, the expression "nucleotide sequence comprising substitution, deletion, insertion and/or addition of one or several nucleotides" as used herein does not provide any limitation on the number of nucleotides to be substituted, deleted, inserted and/or added, as long as a protein encoded by a polynucleotide consisting of such a nucleotide sequence has desired functions. The number of such nucleotides is around 1 to 9 or around 1 to 4, or alternatively, a larger number of nucleotides may be substituted, deleted, inserted and/or added as long as such a mutation allows encoding of the same or a functionally similar amino acid sequence. Likewise, the expression "amino acid sequence comprising substitution, deletion, insertion and/or addition of one or several amino acids as used herein does not provide any limitation on the number of amino acids to be substituted, deleted, inserted and/or added, as long as a protein having such an amino acid sequence has desired functions. The number of such amino acids is around 1 to 9 or around 1 to 4, or alternatively, a larger number of amino acids may be substituted, deleted, inserted and/or added as long as such a mutation provides a functionally similar amino acid. Means for preparing a polynucleotide or protein having such a nucleotide or amino acid sequence are well known to those skilled in the art.

As used herein to describe an amino acid sequence, the term "high identity" refers to a sequence identity of at least 60% or more, preferably 70% or more, more preferably 80% or more, even more preferably 90% or more, and most preferably 95% or more.

Search and analysis for identity between nucleotide or amino acid sequences may be accomplished by using any algorithm or program (e.g., BLASTN, BLASTP, BLASTX, ClustalW) well known to those skilled in the art. In the case of using a program, parameters may be set as required by those skilled in the art, or alternatively, default parameters specific for each program may be used. Detailed procedures for such analysis are also well known to those skilled in the art.

The polynucleotide of the present invention can be obtained from natural products by using techniques such as hybridization and polymerase chain reaction (PCR).

The polynucleotide of the present invention is preferably derived from the genus *Trichoderma*, more preferably *Trichoderma viride*.

The present invention also provides a recombinant vector carrying the polynucleotide of the present invention, as well as a transformant (e.g., a transformed *E. coli*, yeast or insect cell) transformed with the recombinant vector. The present invention further provides a transformation method comprising the step of transforming a host (e.g., an *E. coli*, yeast or insect cell) by using the polynucleotide of the present invention (e.g., the step of transforming a host with the recombinant vector of the present invention).

There is no particular limitation on the vector into which the polynucleotide of the present invention is inserted, as long as it allows expression of the insert in a host. Such a vector generally has a promoter sequence, a terminator sequence, a sequence for inducible expression of an insert in response to external stimulation, a sequence recognized by a restriction enzyme for insertion of a target gene, and a sequence encoding a marker for transformant selection. To create such a recombinant vector and to effect transformation with such a recombinant vector, techniques well known to those skilled in the art may be applied.

[Glycosyltransferase Proteins]

The present invention also provides a novel glycosyltransferase protein and a homolog thereof, i.e., a protein comprising (i), (j) or (k) shown below (preferably a protein consisting of (i), (j) or (k) shown below):

(i) a protein which consists of the amino acid sequence shown in SEQ ID NO: 10;

(j) a protein which consists of an amino acid sequence comprising substitution, deletion, insertion and/or addition of one or several amino acids in the amino acid sequence shown in SEQ ID NO: 10 and which has glycosylation activity on a flavonoid compound; or (k) a protein which consists of an amino acid sequence sharing an identity of at least 60% or more with the amino acid sequence shown in SEQ ID NO: 10 and which has glycosylation activity on a flavonoid compound.

The present invention also provides a mature protein of the above novel glycosyltransferase protein and a homolog thereof, which is modified to remove a putative secretion signal sequence region, i.e., a protein comprising (p), (q) or (r) shown below (preferably a protein consisting of (p), (q) or (r) shown below):

(p) a protein which consists of the amino acid sequence shown in SEQ ID NO: 26;

(q) a protein which consists of an amino acid sequence comprising substitution, deletion, insertion and/or addition of one or several amino acids in the amino acid sequence shown in SEQ ID NO: 26 and which has glycosylation activity on a flavonoid compound; or (r) a protein which consists of an amino acid sequence sharing an identity of at least 60% or more with the amino acid sequence shown in SEQ ID NO: 26 and which has glycosylation activity on a flavonoid compound.

The present invention also provides a protein having glycosylation activity on a flavonoid compound, which is encoded by a polynucleotide being derived from the genus *Trichoderma* (preferably *Trichoderma viride*, *Trichoderma reesei*, *Trichoderma saturnisporum*, *Trichoderma ghanense*, *Trichoderma koningii*, *Trichoderma hamatum*, *Trichoderma harzianum* or *Trichoderma polysporum*) and comprising any one of the nucleotide sequences shown in SEQ ID NOs: 11 to 24. A preferred example of such a protein is a protein having glycosylation activity on a flavonoid compound, which is encoded by a polynucleotide comprising any one of the nucleotide sequences shown in SEQ ID NOs: 11 to 24 and sharing high identity with the nucleotide sequence shown in SEQ ID NO: 6, 9 or 25.

The protein of the present invention can be isolated and purified from a culture supernatant obtained by culturing a species belonging to the genus *Trichoderma*, such as *Trichoderma viride*, *Trichoderma reesei*, *Trichoderma saturnisporum*, *Trichoderma ghanense*, *Trichoderma koningii*, *Trichoderma hamatum*, *Trichoderma harzianum* or *Trichoderma polysporum* in a known culture solution. Alternatively, the protein of the present invention can also be obtained as a recombinant protein from a transformant (e.g., a transformed yeast or *E. coli* cell) transformed with a recombinant vector carrying the polynucleotide of the present invention.

[Enzymological Properties of Enzyme TRa2]

Among novel enzyme proteins provided by the present invention, particularly preferred is a glycosyltransferase consisting of the amino acid sequence shown in SEQ ID NO: 10 (herein also referred to as "TRa2"), which is obtained from the culture supernatant of *Trichoderma viride* strain IAM5141. This enzyme has the following enzymological features in reaction between flavonoid and glycosyl donor.

Glycosyl Donor Selectivity:

Under the conditions shown in the Example section, this enzyme uses maltotriose, maltotetraose, maltopentaose, maltohexaose, maltoheptaose, soluble starch, dextrin, γ-cyclodextrin or the like as a glycosyl donor, but does not target cellobiose, dextran, maltose monohydrate, carboxymethylcellulose sodium salt, isomaltooligosaccharide, α-cyclodextrin, β-cyclodextrin or the like as a glycosyl donor. Moreover, this enzyme is a glycosyltransferase capable of producing not only sugars composed of one or two glucose molecules, but also glycosides whose sugar chain length is three (G3) or more glucose molecules.

Substrate Specificity:

This enzyme can act on and glycosylate a wide range of polyphenols including major flavonoid members such as catechin, epigallocatechin gallate, naringenin, quercetin, daidzein, genistein and kaempferol, as well as esculetin.

Optimum Reaction Temperature and pH (Reaction Temperature Dependence and pH Dependence):

In the case of hydrolysis reaction, this enzyme allows a satisfactory reaction at a temperature of about 20° C. to about 60° C., particularly about 35° C. to about 55° C., or at a pH of about 4.0 to about 7.0, particularly about 4.5 to about 5.5, under the conditions shown in the Example section.

Likewise, in the case of glycosyltransferase reaction, this enzyme allows a satisfactory reaction at a temperature of about 20° C. to about 60° C., particularly about 45° C. to about 55° C., or at a pH of about 4.0 to about 9.0, particularly about 4.5 to about 7.0, under the conditions shown in the Example section.

Temperature Stability and pH Stability:

Under the conditions shown in the Example section, this enzyme is not deactivated either by treatment at about 20° C. to about 45° C. for 1 hr or by treatment at about pH 5.0 to 9.0 at room temperature for 16 hr.

[Method for Preparing a Glycoside of a Flavonoid Compound]

The present invention also provides a method for preparing a glycoside of a flavonoid compound, which comprises allowing the novel glycosyltransferase of the present invention to act on a mixture of the flavonoid compound and a glycosyl donor (preferably dextrin, soluble starch or γ-cyclodextrin).

Glycosides of flavonoid compounds provided by the present invention have the following formula:

[Formula 1]

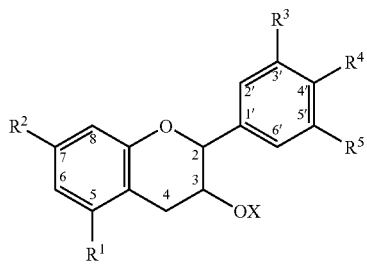

Formula (I)

wherein
at least one of $R^1$ to $R^5$ represents a sugar residue, and each of the others represents OH or $OCH_3$, or
at least one of $R^1$ to $R^4$ represents a sugar residue and each of the others represents OH or $OCH_3$, and $R^5$ represents H; and
X represents H, $CH_3$, a galloyl group or a methylated galloyl group.

This formula further encompasses the glycosides of flavonoid compounds listed below:
5-O-(4-O-α-D-glucopyranosyl-α-D-glucopyranosyl)-(+)-catechin;
5-O-α-D-glucopyranosyl-(+)-catechin;
4'-O-(4-O-α-D-glucopyranosyl-α-D-glucopyranosyl)-(+)-catechin;
4'-O-α-D-glucopyranosyl-(+)-catechin;
3'-O-(4-O-α-D-glucopyranosyl-α-D-glucopyranosyl)-(+)-catechin;
3'-O-α-D-glucopyranosyl-(+)-catechin;
7-O-α-D-glucopyranosyl-(−)-epigallocatechin-3-O-gallate;
7-O-(4-O-α-D-glucopyranosyl-α-D-glucopyranosyl)-(−)-epigallocatechin-3-O-gallate;
3'-O-α-D-glucopyranosyl-(−)-epigallocatechin-3-O-gallate; and
3'-O-(4-O-α-D-glucopyranosyl-α-D-glucopyranosyl)-(−)-epigallocatechin-3-O-gallate, as well as optical isomers thereof.

[Uses of Glycosides]

Glycosides obtained by the present invention can be used as food compositions, pharmaceutical compositions or cosmetic compositions. More specifically, for example, such a composition incorporating a glycoside of a catechin compound can be used as an agent for the following purposes, as in the case of catechin: anti-allergy, anti-oxidation, anti-cancer, anti-inflammation, anti-bacteria/anti-caries, anti-virus, detoxication, intestinal flora improvement, odor elimination, anti-hypercholesterolemia, anti-hypertension, anti-hyperglycemia, anti-thrombosis, dementia prevention, body fat burning, inhibition of body fat accumulation, endurance improvement, anti-fatigue or renal function improvement, or alternatively, can also be used as a food composition, a pharmaceutical composition or a cosmetic composition.

Food compositions include nutritional supplementary foods, health foods, therapeutic dietary foods, general health foods, supplements and beverages. Beverages include tea beverages, juices, soft drinks, and drinkable preparations.

Pharmaceutical compositions may be prepared as drugs or quasi drugs, preferably oral formulations or dermatologic external preparations, and may be provided in the form of solutions, tablets, granules, pills, syrups, lotions, sprays, plasters or ointments. Cosmetic compositions may be provided in the form of creams, liquid lotions, emulsion lotions or sprays.

The amount of glycoside(s) incorporated into the food, pharmaceutical or cosmetic composition of the present invention is not limited in any way and may be determined as required by those skilled in the art in consideration of, e.g., solubility and taste by referring to preferred daily intakes of the corresponding flavonoid compound(s). For example, the amount of the glycoside(s) of the present invention incorporated into a composition may be set to 0.01% to 99.9% by weight or may be determined such that the glycoside(s) of the present invention can be given 100 mg to 20 g per day as a single dose or in divided doses (e.g., three doses).

The food, pharmaceutical or cosmetic composition of the present invention may further comprise various ingredients acceptable for food, pharmaceutical or cosmetic purposes. Examples of these additives and/or ingredients include vitamins, saccharides, excipients, disintegrating agents, binders, lubricants, emulsifiers, isotonizing agents, buffers, solubilizers, antiseptics, stabilizers, antioxidants, coloring agents, correctives, flavorings, coagulating agents, pH adjustors, thickeners, tea extracts, herbal extracts, and minerals.

[Other Embodiments]

In the present invention, a glycosyltransferase protein can be immobilized on an appropriate carrier for use as an immobilized enzyme. As a carrier, any conventional resin used for the same purpose may be used, including basic resins (e.g., MARATHON WBA (Dow Chemical), SA series, WA series or FP series (Mitsubishi Chemical Corporation, Japan), and Amberlite IRA904 (Organo)), as well as hydrophobic resins (e.g., Diaion FPHA13 (Mitsubishi Chemical Corporation, Japan), HP series (Mitsubishi Chemical Corporation, Japan), and Amberlite XAD7 (Organo)). In addition, other resins such as Express-Ion D (Whatman), DEAE-Toyopearl 650M (Tosoh Corporation, Japan) and DEAE-sepharose CL4B (Amersham Biosciences) may be preferred for use. Any conventional technique can be used for enzyme immobilization, as exemplified by physical adsorption, the binding method which uses ionic or covalent binding for immobilization, the crosslinking method which uses a reagent having a divalent functional group for immobilization through crosslinking, and the entrapping method which embeds an enzyme within a gel or semipermeable membrane of network structure. For example, immobilization may be accomplished by allowing an enzyme (20 to 2,000 mg, e.g., 50 to 400 mg) in distilled water to be adsorbed to 5 ml of each resin, followed by removal of the supernatant and drying.

The present invention also provides a method for determining the nucleotide sequence of a polynucleotide encoding a protein having glycosylation activity on a flavonoid compound or the amino acid sequence of a protein having glycosylation activity on a flavonoid compound, which comprises using all or part of the nucleotide or amino acid sequence shown in any one of SEQ ID NO: 6, SEQ ID NO: 9, SEQ ID NO: 10 and SEQ ID NOs: 11 to 26.

Advantages of the Invention

The present invention provides novel enzymes which allow efficient glycosylation of flavonoid, as well as genes thereof.

The novel enzymes of the present invention allow glycosylation of flavonoid compounds to thereby improve their water solubility. This suggests that the present invention can enhance the oral absorption of flavonoid compounds. Moreover, improved water solubility will contribute to not only improvement of dissolution rate in water, but also improvement of absorption rate in the body. Thus, the present invention allows flavonoid compounds to exert their useful activity (e.g., antioxidative activity) in vivo with high efficiency.

The present invention can also modify the taste of flavonoid compounds through glycosylation. Particularly when a flavonoid compound having bitter and astringent tastes like a catechin compound is glycosylated in accordance with the present invention, such tastes can be reduced.

The present invention can also improve the heat stability of flavonoid through glycosylation.

BRIEF DESCRIPTION OF THE DRAWINGS

FIG. 3 discloses SEQ ID NOS 29-32, respectively, in order of appearance.

FIG. 5 shows the cDNA nucleotide sequence of TRa2 (SEQ ID NO: 9) and its corresponding deduced amino acid sequence (SEQ ID NO: 10). The double-underlined part represents a putative secretion signal sequence.

FIG. 6 shows a comparison of the primary structure between the deduced amino acid sequence of TRa2 (SEQ ID NO: 10) and the Taka-amylase precursor amino acid sequence (GB No. BAA00336) (SEQ ID NO: 27). Underlined: putative secretion signal of TRa2; broken-underlined: secretion signal of Taka-amylase; double-underlined: 4 regions highly conserved among α-amylase family enzymes; and amino acid residues indicated with *: amino acid residues located at catalytic sites.

FIG. 8 discloses SEQ ID NOS 33 and 11-24, respectively, in order of appearance.

EXAMPLES

Example 1

Catechin Glycosylation Activity in *Trichoderma* Culture

Figure 1:
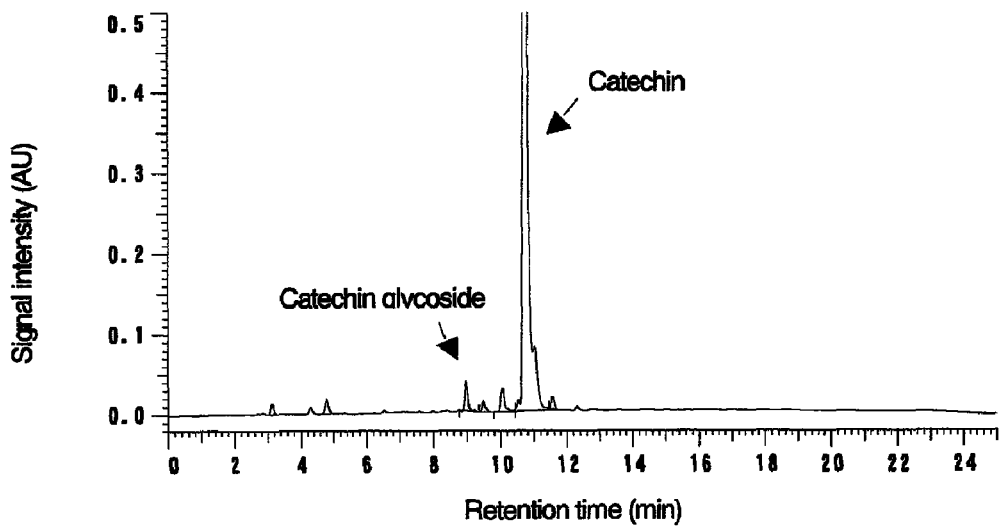
FIG. 1 shows an HPLC analysis chart of catechin when treated with a crude enzyme solution of *Trichoderma viride* IAM5141.

*Trichoderma viride* strain IAM5141 was inoculated from a slant into a liquid medium (10 ml) containing 1% yeast extract (Difco), 1% polypeptone (Nihon Pharmaceutical Co., Ltd., Japan) and 2% dextrin (Nacalai Tesque, Inc., Japan), followed by shaking culture at 30° C. for 1 day to give a pre-cultured solution. Further, the entire volume of the pre-cultured solution was inoculated into 900 ml of the same liquid medium and cultured at 30° C. for 3 days, followed by filter filtration to prepare a culture supernatant solution. After addition of ammonium sulfate (387 g, 80% saturation) to the culture supernatant (690 ml), the mixture was stirred and centrifuged to collect a precipitate. The resulting precipitate was diluted with 10 ml of 0.1 M acetate buffer (pH 5.0) for use as a crude enzyme solution.

To the crude enzyme solution (100 µl), catechin (3 mg) and dextrin (10 mg) were added and stirred at 50° C. for 24 hours to cause an enzyme reaction. The reaction solution was diluted 10-fold with 0.1% trifluoroacetic acid (TFA), 10 µl of which was then analyzed by high performance liquid chromatography (HPLC).

Analysis Conditions
Column: Develosil C30-UG-5 (4.6×150 mm)
Gradient conditions: 5% Eluent B→50% Eluent B/20 min
Eluent A: 0.1% TFA/distilled water
Eluent B: 90% acetonitrile/0.08% TFA
Flow rate: 1 ml/min
Detection wavelength: 280 nm As shown in FIG. 1, the results confirmed the generation of a catechin glycoside through the above reaction. Moreover, it was also confirmed that a similar glycoside was generated in the case of using γ-cyclodextrin as a glycosyl donor. These results suggest that *T. viride* strain IAM5141 produces and secretes an enzyme which glycosylates catechin using dextrin or γ-cyclodextrin as a glycosyl donor.

Example 2

PCR Cloning of Partial α-Amylase Homolog Sequences

In view of the facts that dextrin and γ-cyclodextrin are polymers in which glucose residues are linked through α-1,4 linkages and that the intended enzyme has the ability to degrade these polymers, it is suggested that the enzyme may be an α-amylase family-like enzyme.

Figure 2:
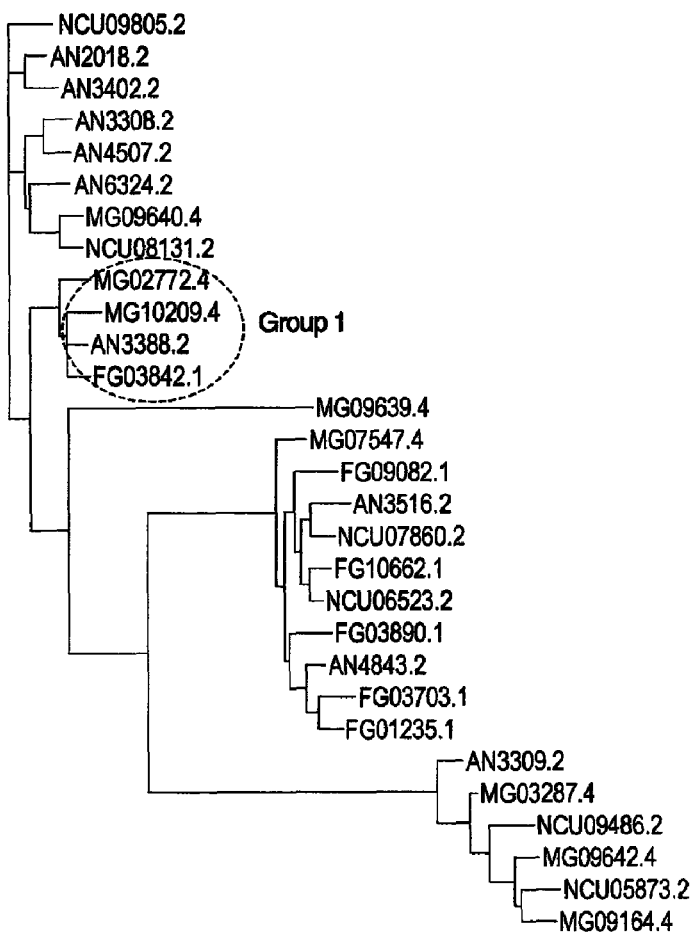
FIG. 2 shows a dendrogram prepared by a dendrogram preparation program, Tree view, with respect to the amino acid sequences of putative ORFs having the alpha-amylase catalytic domain (accession No. PF00128) motif extracted from the genomic information databases of *Aspergillus nidulans, Neurospora crassa, Magnaporthe grisea* and *Fusarium graminearum*.
Figure 3:
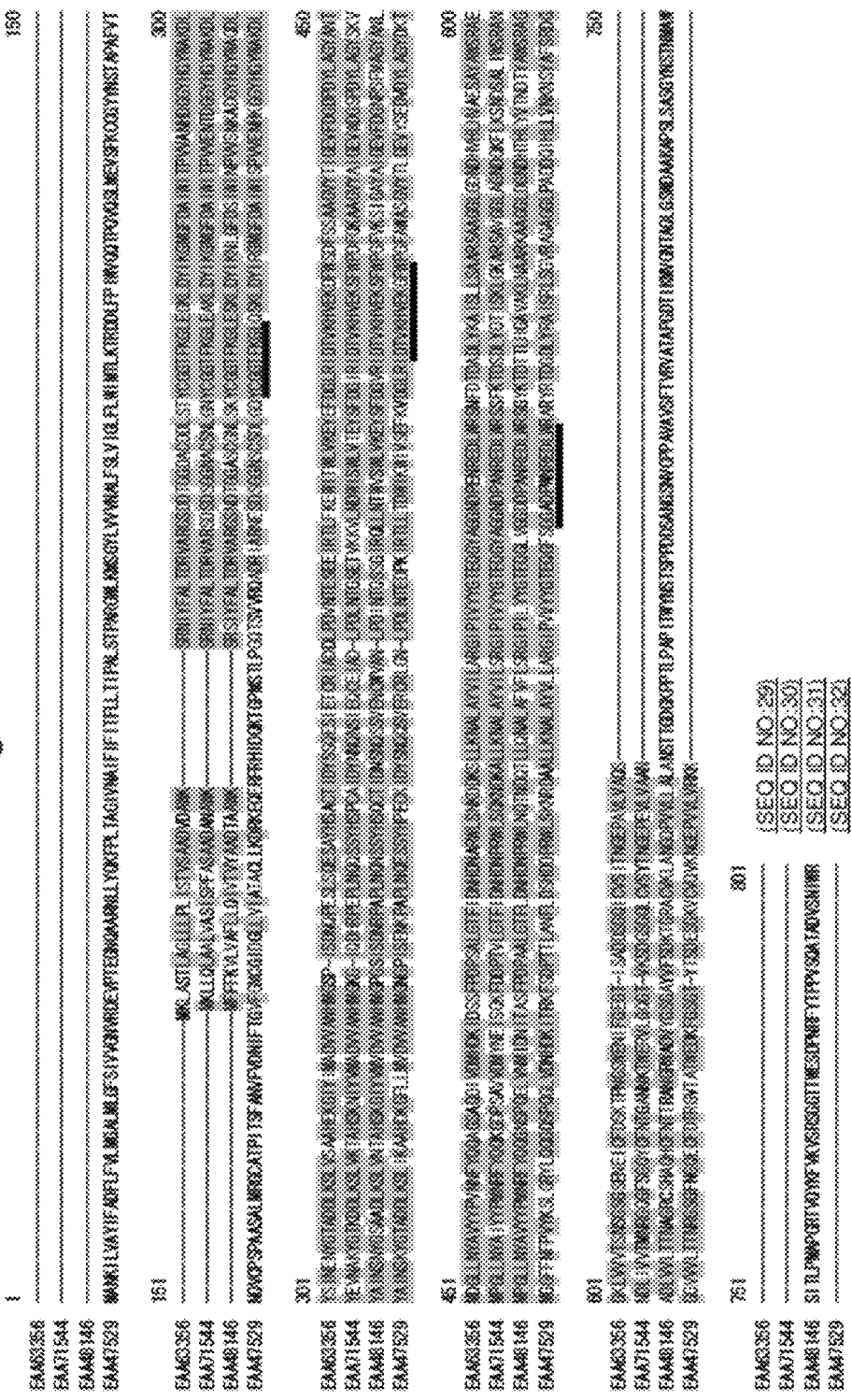
FIG. 3 shows an alignment of 4 amino acid sequences in Group 1 of FIG. 2, along with their highly conserved regions (underlined).

For further study, with respect to a putative ORF having the alpha-amylase catalytic domain (accession No. PF00128) motif in the protein family database (PFAM), 9, 6, 8 and 6 amino acid sequences were extracted from the genomic information databases of *Aspergillus nidulans, Neurospora crassa, Magnaporthe grisea* and *Fusarium graminearum*, respectively, among microorganisms belonging to the same ascomycetous filamentous fungi as *Trichoderma* and already identified for their genome sequences. For these sequences, an alignment was prepared by the homology search program ClustalW and a dendrogram was prepared by the dendrogram preparation program Tree view, whereby the sequences were grouped on the basis of their homology. Four amino acid sequences in Group 1 of FIG. 2, i.e., MG02772.4 (EAA47529), MG10209.4 (EAA48146), AN3388.2 (EAA63356) and FG03842.1 (EAA71544) (numbers in parentheses are Genebank Accession Nos.) were aligned to synthesize oligo DNAs corresponding to the amino acid sequences of their highly conserved regions (FIG. 3, underlined).

```
AMY-12f:
5'-TAYTGYGGNGGNACNTTYAARGGNYT-3'    (SEQ ID NO: 1)

AMY-15r:
5'-TTYTCNACRTGYTTNACNGTRTCDAT-3'    (SEQ ID NO: 2)

AMY-17r:
5'-GGTNAYRTCYTCNCKRTTNGCNGGRTC-3'   (SEQ ID NO: 3)
```

From wet cells (about 1 g) of *T. viride* IAM5141 cultured as described above, genomic DNA was extracted with a DNeasy plant Maxi Kit (QIAGEN). This genomic DNA (50 ng) was used as a template to perform PCR reaction with primers AMY-12f and AMY-15r or primers AMY-12f and AMY-17r. Namely, PCR was accomplished by using ExTaq (Takara Bio Inc., Japan) under the following conditions: 94° C. for 2 minutes, (94° C. for 1 minute, 50° C. for 1 minute, 72° C. for 1 minute)×30 cycles, and 72° C. for 10 minutes. The PCR products were analyzed by agarose gel electrophoresis, confirming a fragment of approximately 0.6 kbp for the primer combination of AMY-12f and AMY-15r and a fragment of approximately 1.0 kbp for the primer combination of AMY-12f and AMY-17r. Then, these DNA fragments were excised from the agarose gel and purified with a GFX PCR DNA and Gel Band Purification Kit (Amersham Biosciences). Each DNA was cloned with a TOPO-TA cloning kit (Invitrogen) and analyzed for its nucleotide sequence using an ABI 3100 Avant (Applied Biosystems). The nucleotide sequence obtained for the former fragment was included within the nucleotide sequence obtained for the latter fragment. A homology search with Blastx was made for this nucleotide sequence against amino acid sequences registered in GenBank, indicating that the highest homology was observed with MG10209.4 (EAA48146).

Example 3

Genome Sequence Determination of α-Amylase Homolog

On the basis of the resulting nucleotide sequence of approximately 1.0 kbp, the following primers were designed and used to perform Inverse PCR.

```
TRa2-2:
5'-CCAACCTGGTATCTACATAC-3'    (SEQ ID NO: 4)

TRa2-3:
5'-AGATGGCATCAAATCCCAT-3'     (SEQ ID NO: 5)
```

Figure 4:
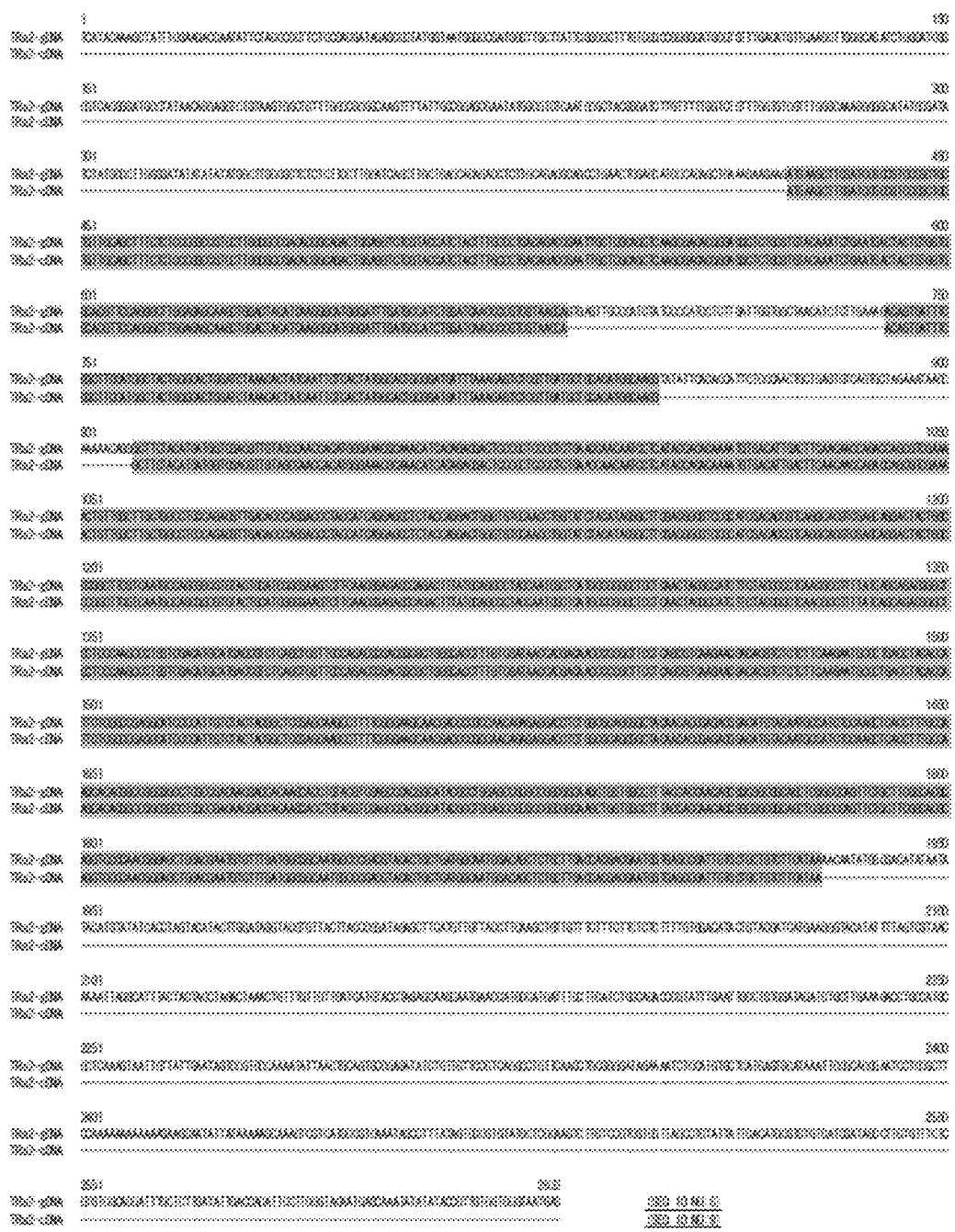
FIG. 4 shows a comparison between genomic DNA sequence (SEQ ID NO: 6) and cDNA sequence (SEQ ID NO: 9) of TRa2.

First, the genomic DNA prepared from *T. viride* IAM5141 was completely digested with HindIII or PstI, and then closed by self-ligation through overnight incubation at 16° C. with ligation high (Toyobo Co., Ltd., Japan). These DNAs (0.1 μg each) were each used as a template to perform PCR reaction with the above primers TRa2-2 and TRa2-3. PCR was accomplished by using LA Taq (Takara Bio Inc., Japan) under the following conditions: 94° C. for 2 minutes, (95° C. for 30 seconds, 66° C. for 15 minutes)×30 cycles, and 72° C. for 10 minutes. The resulting PCR products were analyzed by agarose gel electrophoresis, confirming a DNA fragment of approximately 2 kb for the case of using the HindIII-digested genomic DNA as a template, and a DNA fragment of approximately 4.5 kb for the case of using the PstI-digested genome as a template. These DNA fragments were each excised from the agarose gel and cloned in the same manner as described above. Nucleotide sequences were determined from both ends of the inserted fragments. The nucleotide sequences from the HindIII-digested genome and the PstI-digested genome were found to overlap with each other until reaching the restriction enzyme sites. The nucleotide sequences thus obtained were ligated to the partial sequence previously obtained. This nucleotide sequence is shown in FIG. 4 (TRa2-gDNA) and SEQ ID NO: 6. The coding region of the α-amylase homolog was deduced by comparison with the 4 sequences in Group 1 of FIG. 2, appearance of an initiation codon and a termination codon, etc. The initiation codon was considered to be ATG at nucleotides 423-425, while the termination codon was considered to be TAA at nucleotides 1926-1928.

Example 4 cDNA Cloning of α-Amylase Homolog

From the cells of *T. viride* strain IAM5141 cultured as described above (about 0.1 g), total RNA was extracted with an RNeasy plant mini kit. The total RNA (1 μg) was used for cDNA synthesis in a SuperScript First-Strand system for RT-PCR (Invitrogen) using random hexamers.

On the basis of the genome sequence previously obtained, the following primers were designed.

```
TRa2EcoRI-f2:
5'-GGAATTCATGAAGCTTCGATCCGCCGTCCC-3'   (SEQ ID NO: 7)

TRa2XhoI-r2:
5'-CCGCTCGAGTTATGAAGACAGCAGCACAAT-3'   (SEQ ID NO: 8)
```

Figures 5, 6:
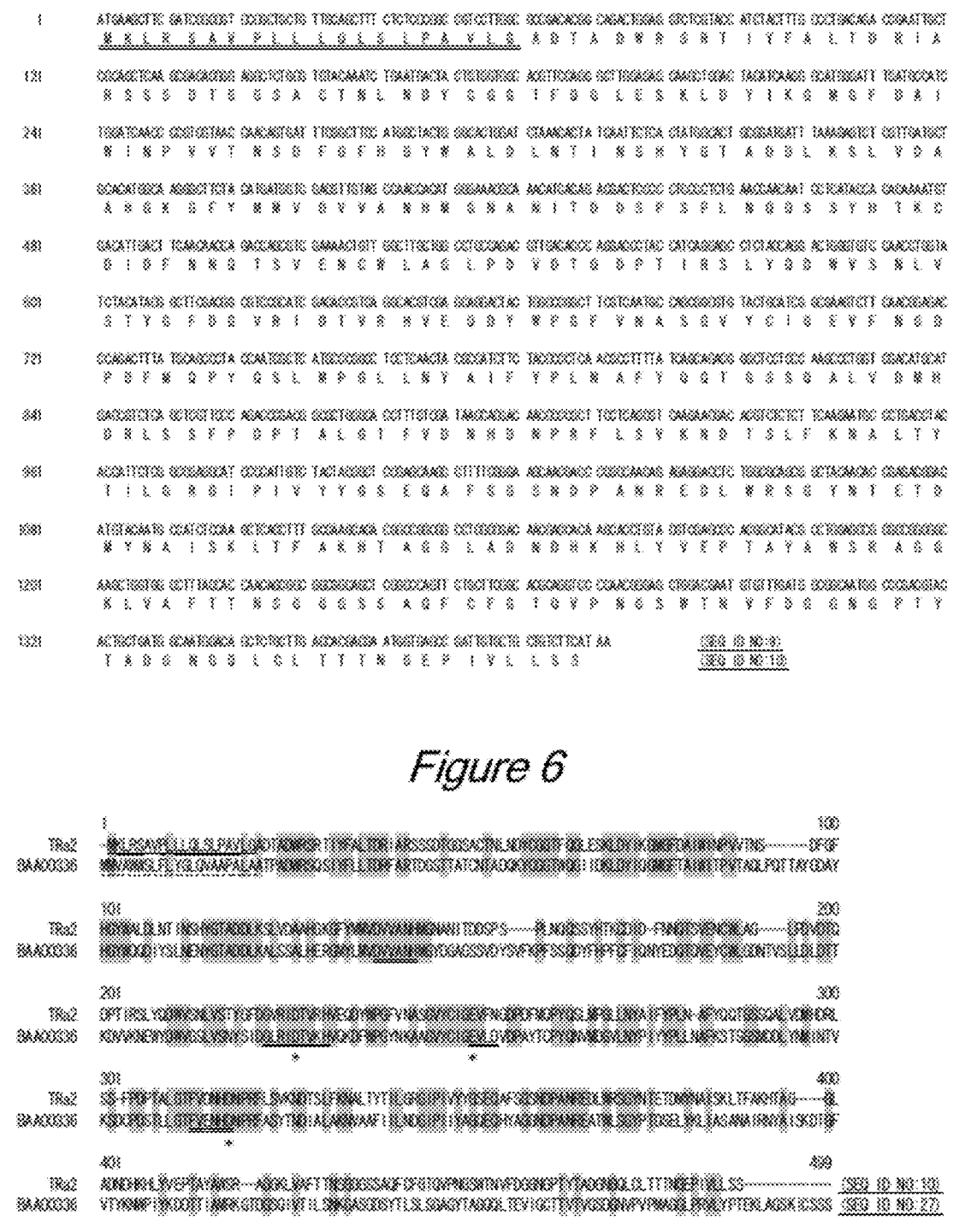

The synthesized cDNA was used as a template to perform PCR reaction with the above primers TRa2EcoRI-f2 and TRa2XhoI-r2. PCR was accomplished by using Ex Taq (Takara Bio Inc., Japan) under the following conditions: 94° C. for 2 minutes, (94° C. for 1 minute, 55° C. for 1 minute, 72° C. for 2 minutes)×30 cycles, and 72° C. for 10 minutes. The resulting PCR products were analyzed by agarose gel electrophoresis, confirming a DNA fragment of approximately 1.5 kb. This DNA fragment was excised from the agarose gel and purified by GFX. The resulting DNA fragment was cloned with a TOPO-TA cloning kit (Invitrogen) to construct plasmid pCRTRa2-cDNA, and the nucleotide sequence of the cDNA was determined (FIG. 4, FIG. 5 and SEQ ID NO: 9). The genomic DNA sequence previously obtained was compared with the cDNA sequence thus obtained, indicating that the genome sequence contained two introns (FIG. 4). The cDNA sequence was found to contain 1392 by ORF encoding a protein composed of 463 amino acid residues (FIG. 5 and SEQ ID NO: 10). This gene was designated as TRa2. When the deduced amino acid sequence encoded by this gene was analyzed by Signal P (Nielsen H. et. al., Protein Eng., 10, 1-6, 1997), the N-terminal 20 amino acid residues appeared to constitute a secretion signal sequence. Further, a homology search was made for the deduced amino acid sequence encoded by TRa2 in the same manner as described above, indicating that the highest homology was observed with AN3388.2 (EAA63356). The deduced amino acid sequence of TRa2 protein was compared with the amino acid sequence of Taka-amylase, which is a known α-amylase. The result indicated that 4 conserved regions among α-amylase family enzymes were also conserved in this enzyme (FIG. 6, double-underlined), and that the aspartic acid residue, the glutamic acid residue and the aspartic acid residue, each serving as an active center, were all conserved (FIG. 6, amino acid residues indicated with *).

Example 5

Construction of Secretory Expression System for TRa2 Protein in Yeast

The plasmid pCRTRa2-cDNA was digested with restriction enzymes EcoRI and XhoI to give a fragment of approximately 1.5 kb, which was then ligated to an EcoRI- and SalI-digested fragment of plasmid pYE22m (Biosci. Biotech. Biochem., 59(7), 1221-1228, 1995) using ligation high (Toyobo Co., Ltd., Japan) to thereby obtain plasmid pYETRa2.

The plasmid pYETRa2 was used to transform yeast S. cerevisiae strain EH1315 by the lithium acetate method. The resulting transformed strain was designated as strain TRa2-1. A loopful of the strain TRa2-1 was inoculated into 10 ml YPD (Difco) liquid medium and cultured with shaking at 30° C. for 2 days. Since the TRa2 protein has a secretion signal sequence composed of 20 amino acid residues at its N-terminal end, the protein was considered to be secreted into a culture solution. Then, the yeast cells were precipitated by centrifugation to collect the culture supernatant.

Example 6

Measurement of Glycosidase Activity of TRa2

The culture supernatant (500 μl) was concentrated about 5-fold using Microcon YM-30 (Amicon). The above concentrate (10 μl) was added to 100 μl of 20 mM acetate buffer (pH 5.0) containing 0.5% maltose, maltotriose, maltotetraose, dextrin, α-cyclodextrin, β-cyclodextrin or γ-cyclodextrin, and reacted at 50° C. for 1 hour.

After completion of the reaction, each sample was analyzed by TLC as follows. The plate used was a silica gel G-60 plate (Merck & Co., Inc.), and the developing solution used was 2-propanol:acetone:0.5 M lactic acid=2:2:1. For detection, the plate was sprayed with sulfuric acid:ethanol=1:9, air-dried and then heated on a hot plate. As a result, none of the sugars was degraded in a culture solution of the control strain (strain C-1) transformed with vector pYE22m. In contrast, in a culture solution of the strain TRa2-1, maltotriose, maltotetraose, dextrin and γ-cyclodextrin were degraded to mainly generate maltose and glucose, but there was no degradation of maltose, α-cyclodextrin and β-cyclodextrin.

Example 7

Measurement of Glycosylation Activity of TRa2

Figure 7:
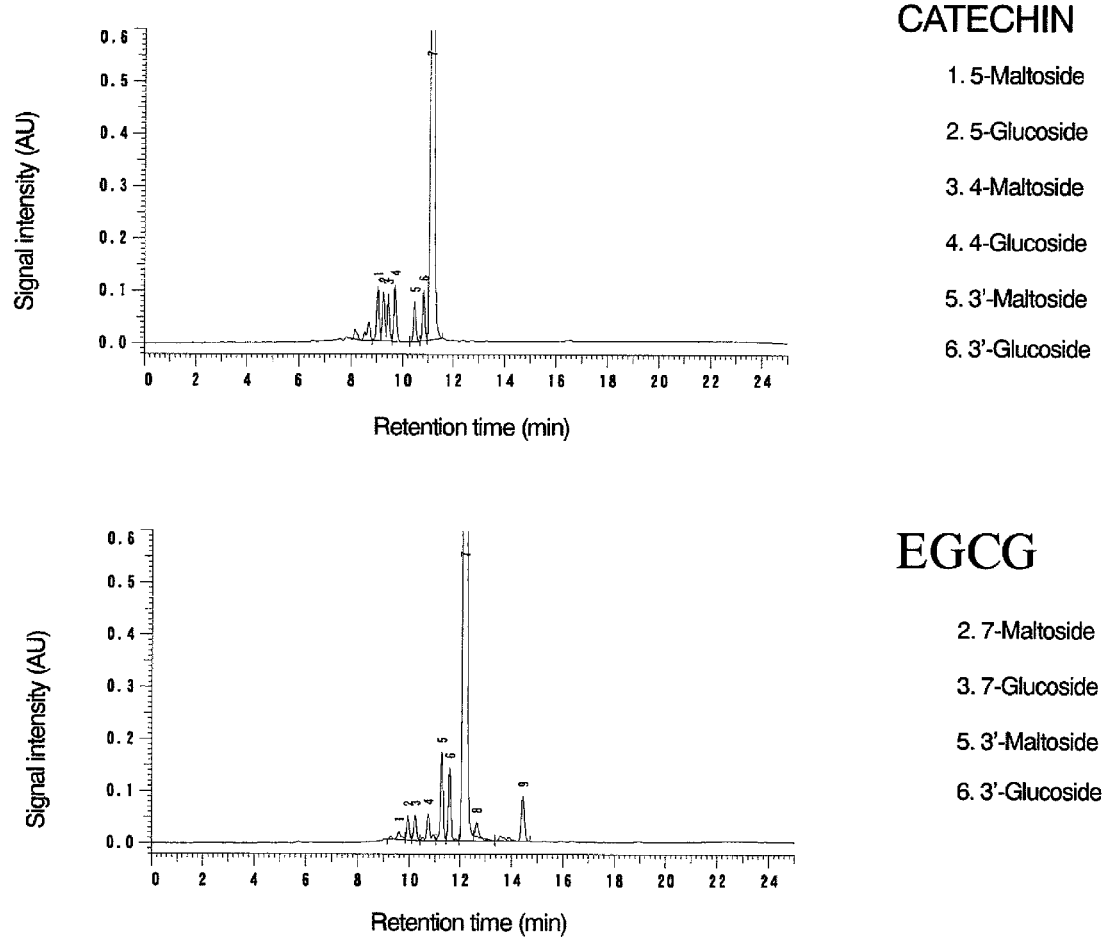
FIG. 7 shows HPLC analysis charts of the reaction solution when (+)-catechin or (−)-epigallocatechin-3-O-gallate and dextrin were added to and reacted in a culture supernatant stock of *T. viride* IAM5141 or a concentrate thereof.

To 100 μl of a culture supernatant stock or a concentrate thereof concentrated about 5-fold with a VIVASPIN 10,000 MWCO/PES (VIVASCIENCE), (+)-catechin or (−)-epigallocatechin-3-O-gallate (3 mg) and dextrin (10 mg) were added and reacted with stirring at 50° C. for 1 day. After completion of the reaction, the reaction solution was diluted 10-fold with a 0.1% trifluoroacetic acid solution and analyzed by high performance liquid chromatography (HPLC) under the same conditions as used in Example 1. As a result, no reaction product was observed in the reaction solution reacted with the culture supernatant from the control strain (strain C-1) transformed with vector pYE22m, whereas the generation of catechin glycosides and epigallocatechin-3-O-gallate glycosides was confirmed in the case of the strain TRa2-1 (FIG. 7).

Example 8

TRa2-Catalyzed Preparation of Catechin Glycosides

The strain TRa2-1 was inoculated into 200 ml YPD liquid medium and cultured with shaking at 30° C. for 3 days. The cells were collected by centrifugation to obtain the culture supernatant. This culture supernatant (100 ml) was concentrated to 50 ml using a ultrafiltration disk NMWL 30000/ regenerated cellulose while adding 100 ml of 0.1 M acetate buffer (pH 5), and used as a TRa2 enzyme solution. The above TRa2 enzyme solution (50 ml) was mixed with (+)-catechin (1.5 g) and dextrin (5 g), followed by stirring at 45° C. for 18 hr. The reaction solution was centrifuged, and the supernatant was adsorbed onto a LH20 (Amersham Biosciences) resin 60 ml/φ2.5×20 cm column. After elution with distilled water (120 ml) and 10% ethanol (240 ml), glycoside fractions were collected and lyophilized to give 530 mg lyophilized powder, 50 mg of which was then dissolved in 5 ml distilled water and separated on a Develosil C30-UG-5 column 20×250 mm, A: 0.1% TFA/distilled water, B: 90% methanol/0.1% TFA, 30% B, 3 ml/min, 280 nm. Peaks 1 to 6 were collected and lyophilized in the order in which they were eluted from the HPLC column. MS and NMR analyses suggested that Peak 1 was 5-O-(4-O-α-D-glucopyranosyl-α-D-glucopyranosyl)-(+)-catechin, Peak 2 was 5-O-α-D-glucopyranosyl-(+)-catechin, Peak 3 was 4'-O-(4-O-α-D-glucopyranosyl-α-D-glucopyranosyl)-(+)-catechin, Peak 4 was 4'-O-α-D-glucopyranosyl-(+)-catechin, Peak 5 was 3'-O-(4-O-α-D-glucopyranosyl-α-D-glucopyranosyl)-(+)-catechin, and Peak 6 was 3'-O-α-D-glucopyranosyl-(+)-catechin.

5-O-(4-O-α-D-glucopyranosyl-α-D-glucopyranosyl)-(+)-catechin: m/z 615.2, NMR δ ppm (D$_2$O); 2.71 (1H, dd), 2.85 (1H, dd), 3.42 (1H, t), 3.56-3.85 (9H, m), 4.19 (1H, t), 4.26 (1H, dd), 4.87 (1H, d), 5.70 (1H, d), 6.19 (1H, d), 6.39 (1H, d), 6.83 (1H, dd), 6.90-6.93 (2H, m).

5-O-α-D-glucopyranosyl-(+)-catechin: m/z 453.2, NMR δ ppm (D$_2$O); 2.62 (1H, dd), 2.81 (1H, dd), 3.43 (1H, t), 3.45-3.55 (1H, m), 3.6-3.7 (3H, m), 3.83 (1H, t), 4.18 (1H, dd), 4.76 (1H, d), 5.61 (1H, d), 6.09 (1H, d), 6.31 (1H, d), 6.77 (1H, d), 6.8-6.9 (2H, m).

4'-O-(4-O-α-D-glucopyranosyl-α-D-glucopyranosyl)-(+)-catechin: m/z 615.2, NMR δ ppm (D$_2$O); 2.54 (1H, dd), 2.81 (1H, dd), 3.43 (1H, t), 3.60 (1H, dd), 3.68-3.94 (9H, m), 4.19-4.28 (2H, m), 4.82 (1H, d), 5.44 (1H, d), 5.62 (1H, d), 6.04 (1H, d), 6.11 (1H, d), 6.91 (1H, dd), 7.00 (1H, d), 7.22 (1H, d).

4'-O-α-D-glucopyranosyl-(+)-catechin: m/z 453.2, NMR δ ppm (D$_2$O); 2.45 (1H, dd), 2.73 (1H, dd), 3.45 (1H, t), 3.65-3.75 (4H, m), 4.11 (1H, dd), 4.7-4.75 (2H, m), 5.53 (1H, d), 5.95 (1H, d), 6.02 (1H, d), 6.83 (1H, dd), 6.91 (1H, d), 7.15 (1H, d).

3'-O-(4-O-α-D-glucopyranosyl-α-D-glucopyranosyl)-(+)-catechin: m/z 615.2, NMR δ ppm (D$_2$O); 2.54 (1H, dd), 2.80 (1H, dd), 3.44 (1H, t), 3.59 (1H, dd), 3.67-3.90 (9H, m), 4.17-4.24 (2H, m), 4.83 (1H, d), 5.41 (1H, d), 5.55 (1H, d), 6.03 (1H, d), 6.10 (1H, d), 7.10 (1H, d), 7.06 (1H, d), 7.26 (1H, d).

3'-O-α-D-glucopyranosyl-(+)-catechin: m/z 453.2, NMR δ ppm (D$_2$O); 2.43 (1H, dd), 2.73 (1H, dd), 3.27 (1H, s), 3.44 (1H, t), 3.6-3.7 (4H, m), 3.88 (1H, t), 4.10 (1H, dd), 4.69 (1H, d), 5.46 (1H, d), 5.93 (1H, s), 6.01 (1H, s), 6.89 (1H, d), 6.94 (1H, dd), 7.18 (1H, d).

Example 9

TRa2-Catalyzed Preparation of Epigallocatechin-3-O-Gallate Glycosides

The strain TRa2-1 was inoculated into 100 ml YPD liquid medium and cultured with shaking at 30° C. for 3 days. The cells were collected by centrifugation to obtain the culture supernatant. This culture supernatant (45 ml) was concentrated to 20 ml using a ultrafiltration disk NMWL 30000/regenerated cellulose while adding 50 ml of 0.1 M acetate buffer (pH 5), and used as a TRa2 enzyme solution. This TRa2 enzyme solution (20 ml) was mixed with (−)-epigallocatechin-3-O-gallate (600 mg) and dextrin (2 g), followed by stirring at 50° C. for 1 day. The reaction solution was centrifuged, and the supernatant was adsorbed onto a LH20 resin 25 ml/ϕ1.5×30 cm column. After elution with distilled water (100 ml), 10% ethanol (100 ml), 20% ethanol (100 ml) and 30% ethanol (200 ml), the 30% ethanol fraction was collected and lyophilized. The lyophilized powder (120 mg) was dissolved in 12 ml distilled water and separated on a Develosil C30-UG-5 column 20×250 mm, A: 0.1% TFA/distilled water, B: 90% methanol/0.1% TFA, 40% B, 3 ml/min, 280 nm. MS and NMR analyses suggested that Peak 2 was 7-O-(4-O-α-D-glucopyranosyl-α-D-glucopyranosyl)-(−)-epigallocatechin-3-O-gallate, Peak 5 was 3'-O-(4-O-α-D-glucopyranosyl-α-D-glucopyranosyl)-(−)-epigallocatechin-3-O-gallate, and Peak 6 was 3'-O-α-D-glucopyranosyl-(−)-epigallocatechin-3-O-gallate. In contrast, Peak 3 was suggested to be a mixture of glucoside and maltotetraoside, as judged by its MS data (m/z 621.2, 1107.3), and the glucoside was considered to be 7-O-α-D-glucopyranosyl-(−)-epigallocatechin-3-O-gallate, as judged by its retention time.

7-O-(4-O-α-D-glucopyranosyl-α-D-glucopyranosyl)-(−)-epigallocatechin-3-O-gallate: m/z 783.2, NMR δ ppm (CD$_3$OD); 2.88 (1H, dd), 2.01 (1H, dd), 3.26 (1H, t), 3.46 (1H, dd), 3.6-3.9 (9H, m), 4.08 (1H, t), 5.00 (1H, s), 5.20 (1H, d), 5.43 (1H, d), 5.54 (1H, s), 6.27 (1H, d), 6.34 (1H, d), 6.51 (2H, d), 6.94 (2H, d).

3'-O-α-D-glucopyranosyl-(−)-epigallocatechin-3-O-gallate: m/z 621.1, δ ppm (CD3OD); 2.88 (1H, dd), 2.99 (1H, dd), 3.42 (1H, dd), 3.51 (1H, t), 3.69 (1H, m), 3.8-3.9 (3H, m), 4.88 (1H, d), 4.98 (1H, s), 5.49 (1H, broad s), 5.95 (1H, d), 5.96 (1H, d), 6.65 (1H, d), 7.01 (2H, s), 7.11 (1H, d).

3'-O-(4-O-α-D-glucopyranosyl-α-D-glucopyranosyl)-(−)-epigallocatechin-3-O-gallate: m/z 783.2, δ ppm (CD$_3$OD); 2.87 (1H, broad d), 2.99 (1H, dd), 3.27 (1H, t), 3.44-3.48 (2H, m), 3.6-3.8 (4H, m), 3.85 (2H, d), 3.98 (1H, dd), 4.06 (H, t), 4.85 (1H, d), 4.99 (1H, s), 5.28 (1H, d), 5.49 (1H, broad s), 5.94 (1H, d), 5.96 (1H, d), 6.64 (1H, d), 7.01 (2H, s), 7.09 (1H, d).

Example 10

Construction of Yeast Surface Expression System for TRa2 Protein

To express and display a TRa2 protein on the yeast surface, the following vector was constructed. The plasmid pCR-TRa2-cDNA was used as a template to perform PCR reaction with primers TraEcoRI-f2 and TRa2XhoI-r3. PCR was accomplished by using Ex Tag (Takara Bio Inc., Japan) under the following conditions: 94° C. for 2 minutes, (94° C. for 1 minute, 58° C. for 1 minute, 72° C. for 2 minutes)×25 cycles, and 72° C. for 10 minutes. The resulting PCR products were analyzed by agarose gel electrophoresis, confirming a DNA fragment of approximately 1.5 kb.

This DNA fragment was excised from the agarose gel and purified by GFX. The resulting DNA fragment was cloned with a TOPO-TA cloning kit (Invitrogen), confirmed for its nucleotide sequence, and designated as plasmid pCRTRa2-cDNA 2. The plasmid pCRTRa2-cDNA2 was digested with EcoRI and XhoI to give a DNA fragment of approximately 1.5 kb, which was then ligated to an EcoRI- and XhoI-digested DNA fragment (approximately 9.2 kb) of plasmid pGA11 (Appl. Environ. Microbiol., 63, 1362-1366 (1997)) to thereby obtain plasmid pCAS-TRa2.

Example 11

Confirmation of Activity in Yeast Cells Expressing TRa2 Protein on their Surface The plasmid pCAS-TRa2 was used to transform yeast *S. cerevisiae* strain EH1315. The resulting transformed strain was designated as strain TRa2-2. A loopful of the strain TRa2-2 or a control strain (strain C-2) was inoculated into 10 ml YPD liquid medium and cultured at 30° C. for 2 days. The control strain was prepared by transforming yeast *S. cerevisiae* strain EH1315 with plasmid pCAS1 which had been designed to have a multicloning site inserted into plasmid pGA11 between the secretion signal of the glucoamylase gene and a gene encoding the 3'-half of α-agglutinin. The cells were collected by centrifugation, washed with PBS and then suspended in 1 ml PBS. This suspension was used to perform sugar degradation reaction and glycosyltransferase reaction in the same manner as used in Examples 6 and 7, followed by analysis of the reaction products. The results confirmed that the strain TRa2-2 had not only dextrinase activity, but also glycosylation activity on catechin using dextrin as a glycosyl donor, whereas the strain C-2 was free from these activities. Namely, the strain TRa2-2 was shown to display TRa2 in an active form on the yeast surface.

Example 12

Obtaining of TRa2 Homologs from Various Strains of the Genus *Trichoderma*

Figure 8:
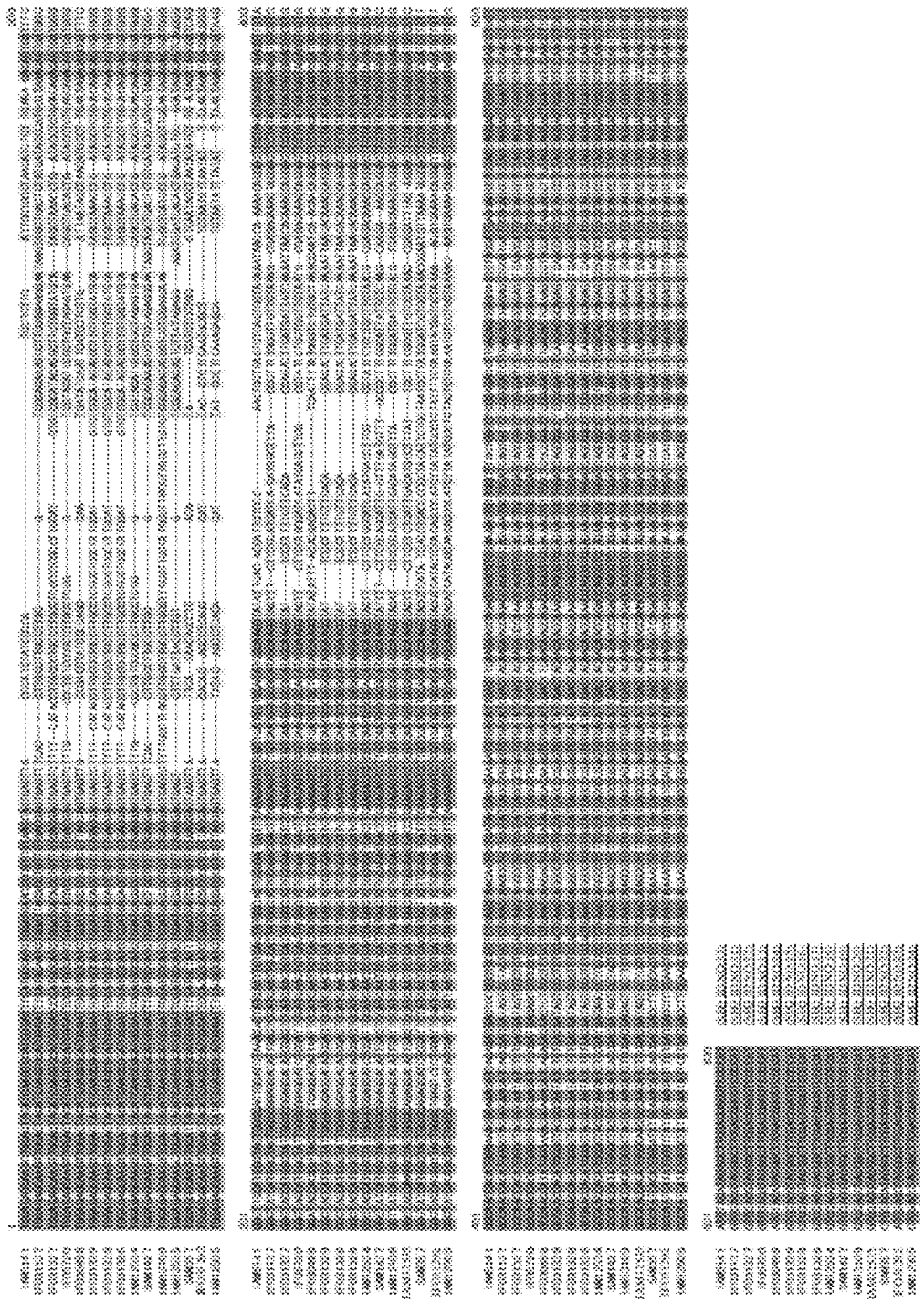
FIG. 8 shows the results of partial nucleotide sequence alignment for TRa2 homologs obtained from genomic DNAs prepared from various strains of the genus *Trichoderma*.

*Trichoderma viride* strain IF031137, *Trichoderma viride* strain SAM1427, *Trichoderma viride* strain IF031327, *Trichoderma viride* strain IF030498, *Trichoderma viride* strain IF05720, *Trichoderma reesei* strain IF031329, *Trichoderma reesei* strain IF031328, *Trichoderma reesei* strain IF031326, *Trichoderma saturnisporum* strain IAM12535, *Trichoderma ghanense* strain IAM13109, *Trichoderma koningii* strain IAM12534, *Trichoderma hamatum* strain IAM12505, *Trichoderma harzianum* strain IF031292 and *Trichoderma polysporum* strain SAM357 were each inoculated into 10 ml liquid medium containing 1% yeast extract (Difco), 1% polypeptone (Nihon Pharmaceutical Co., Ltd., Japan) and 2% dextrin (Nacalai Tesque, Inc., Japan), followed by shaking culture at 30° C. for 4 days. The cells were collected by filter filtration, and genomic DNA was extracted for each strain with a DNeasy plant mini Kit (QIAGEN). This genomic DNA (50 ng) was used as a template to perform PCR reaction with primers AMY-12f and AMY-15r. Namely, PCR was accomplished by using ExTaq (Takara Bio Inc., Japan) under the following conditions: 94° C. for 2 minutes, (94° C. for 1 minute, 50° C. for 1 minute, 72° C. for 1 minute)×30 cycles, and 72° C. for 10 minutes. The PCR products were analyzed by agarose gel electrophoresis, confirming a fragment of approximately 0.6 kbp for each strain. These DNA fragments were each excised from the agarose gel and purified with a GFX PCR DNA and Gel Band Purification Kit (Amersham Biosciences). Each DNA was cloned with a TOPO-TA cloning kit (Invitrogen) and analyzed for its nucleotide sequence using an ABI 3100 Avant (Applied Biosystems). As a result, the sequences of SEQ ID NOs: 11 to 24 were obtained. Their alignment results are shown in FIG. 8. The identity between the TRa2 gene and regions corresponding to these sequences or between these sequences was found to be 63% to 99.5%.

On the basis of these sequences, it is possible to obtain TRa2 homologs having the same activity as TRa2 when repeating the same procedure as used for obtaining the TRa2 gene of *T. viride* IAM5141 and its full-length cDNA.

Example 13

Analysis of Substrate Specificity of TRa2

Figure 9:
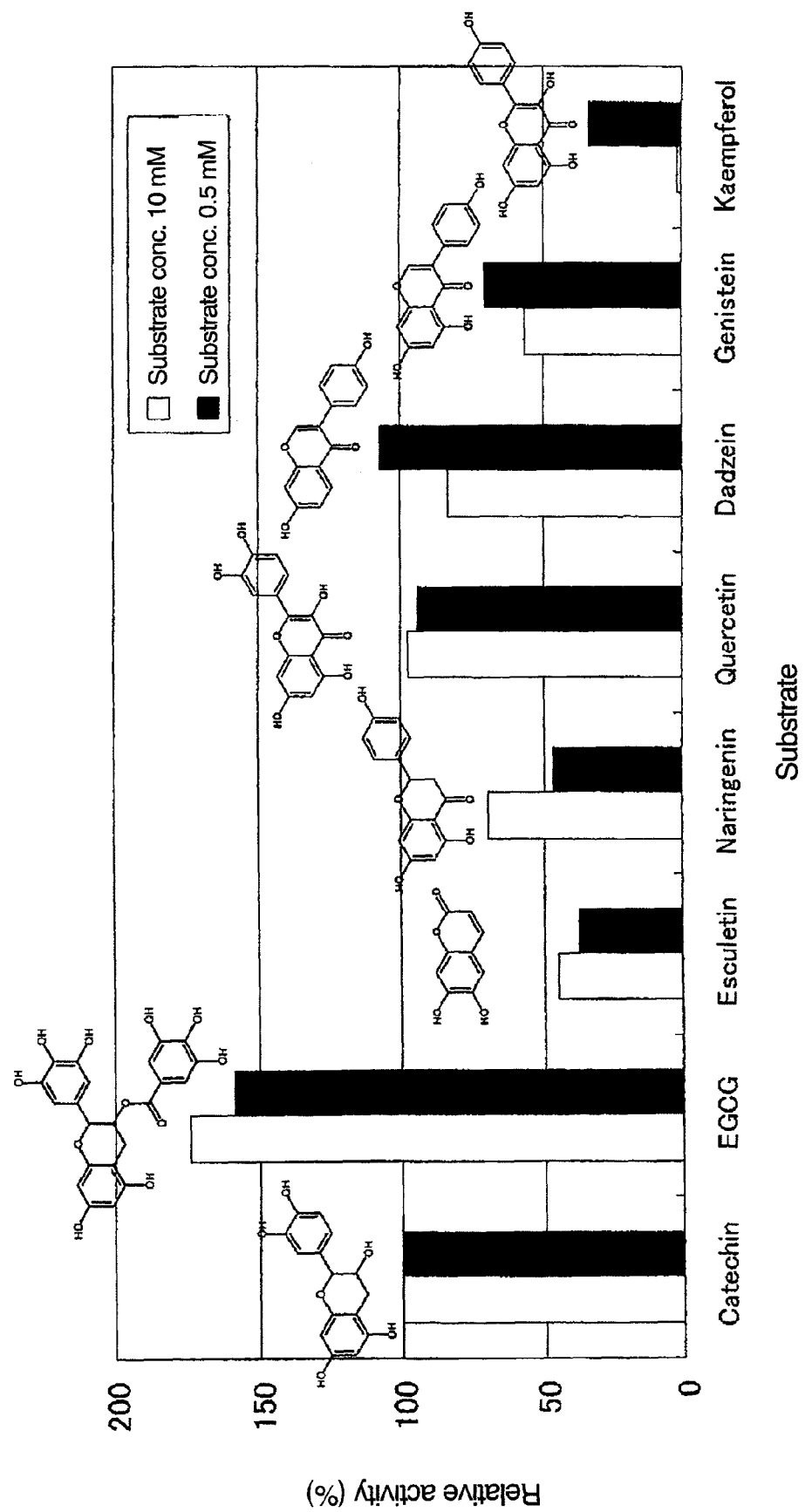
FIG. 9 is a graph showing glycosylation activity of a crude TRa2 enzyme solution prepared from the culture supernatant of a transformant (strain TRa2-1), when used for reaction between each glycosyl acceptor compound ((+)-catechin, (−)-epigallocatechin-3-O-gallate, esculetin, naringenin, quercetin, daidzein, genistein or kaempferol) and dextrin.

The strain TRa2-1 was cultured overnight at 30° C. with shaking in 10 ml YPD medium. After reaching the resting phase, the culture solution was inoculated into the same medium (2% (v/v)) and cultured with shaking at 30° C. for 3 days. After culturing, the supernatant was collected by centrifugation and concentrated 5-fold to give a crude enzyme solution of TRa2. The reaction was performed at 45° C. for 24 hr in 100 µl enzyme reaction solution containing 0.5 mM or 10 mM glycosyl acceptor compound ((+)-catechin, (−)-epigallocatechin-3-O-gallate, esculetin, naringenin, quercetin, daidzein, genistein or kaempferol), 10 mg dextrin, 100 mM acetate buffer (pH 5.2) and the crude enzyme solution, followed by HPLC analysis. The results obtained are shown in FIG. 9.

The area ratio (%) between acceptor compound and glycoside product was 10% for (+)-catechin, 17.7% for (−)-epigallocatechin-3-O-gallate, 3.5% for esculetin, 4.4% for naringenin, 9.4% for quercetin, 10.7% for daidzein, 6.8% for genistein, and 3.1% for kaempferol.

Example 14

Characterization of TRa2

Expression of His-Tagged TRa2 Protein (TRa2-His):
Construction of TRa2-His Expression Plasmid and Obtaining of Transformed Yeast To express a C-terminally His-tagged TRa2 protein in yeast cells, the following primer was designed. TRa2His XhoI-r2: Gctcgagttagtggtggtggtggtggtgtgaagacagcagcaa (SEQ ID NO: 28)

The plasmid pCRTRa2-cDNA was used as a template to perform PCR reaction with primers TraEcoRI-f2 and TRa2HisXhoI-r2. PCR was accomplished by using Ex Taq (Takara Bio Inc., Japan) under the following conditions: 94° C. for 2 minutes, (94° C. for 1 minute, 58° C. for 1 minute, 72° C. for 2 minutes)×25 cycles, and 72° C. for 10 minutes. The resulting PCR products were analyzed by agarose gel electrophoresis, confirming a DNA fragment of approximately 1.5 kb. This DNA fragment was excised from the agarose gel and purified by GFX. The resulting DNA fragment was cloned with a TOPO-TA cloning kit (Invitrogen), confirmed for its nucleotide sequence, and designated as plasmid pCR-TRa2-cDNA-His. pCRTRa2-cDNA-His was digested with EcoRI and XhoI to give a DNA fragment of approximately 1.5 kb, which was then ligated to an EcoRI- and SalI-digested fragment of plasmid pYE22m using ligation high (Toyobo Co., Ltd., Japan) to thereby obtain plasmid pYE-TRa2-His. The plasmid pYE-TRa2-His was used to transform yeast *S. cerevisiae* strain EH1315. The resulting transformed strain was designated as strain TRa2-3.

Culturing

The strain TRa2-3 was cultured in 20 ml SD(-Trp) at 30° C. for 16 hr. The pre-cultured solution was inoculated into 1 L of SD(-Trp)+100 mM $KH_2PO_4$—KOH (pH 6.0) and cultured at 30° C. for 3 days, followed by centrifugation to collect the culture supernatant.

Purification

The culture supernatant was applied onto a $Ni^{2+}$-chelated Chelating Sepharose Fast Flow (5 ml, Pharmacia Biotech) column equilibrated with Buffer S1 [20 mM $NaH_2PO_4$—NaOH (pH 7.4), 10 mM imidazole, 0.5 M NaCl, 15 mM 2-mercaptoethanol], followed by washing with the same buffer (40 ml). Subsequently, proteins bound to the column were eluted with Buffer E1 [20 mM $NaH_2PO_4$—NaOH (pH 7.4), 200 mM imidazole, 0.5 M NaCl, 15 mM 2-mercaptoethanol]. Active fractions were collected, and then desalted and concentrated using a VIVASPIN (30,000 MWCO, VIVASCIENCE).

Subsequently, the enzyme solution was applied (1.5 ml/min) onto a Resource Q (1 ml, Pharmacia Biotech) column equilibrated with Buffer S2 [20 mM $KH_2PO_4$—KOH (pH 7.4), 15 mM 2-mercaptoethanol, 0.1% CHAPS], followed by washing with the same buffer (10 ml). Subsequently, proteins bound to the column were eluted with a 0-100% linear gradient of Buffer E2 [20 mM $KH_2PO_4$—KOH (pH 7.4), 0.6 M NaCl, 15 mM 2-mercaptoethanol, 0.1% CHAPS] (60 ml). Active fractions were collected, and then desalted and concentrated using a VIVASPIN (30,000 MWCO, VIVASCIENCE).

The same procedure was repeated again to perform Resource Q column chromatography. Active fractions showing a single band on SDS-PAGE were collected, and then desalted and concentrated using a VIVASPIN (30,000 MWCO, VIVASCIENCE).

Measurement of Enzyme Activity:
Glycosylation Activity

A reaction solution (100 µl, 10 mM catechin, 10 mg dextrin, 100 mM Acetate-NaOH (pH 5.3), enzyme solution) was stirred at 45° C. for 24 hr, followed by addition of 0.5% TFA (100 µl) to stop the reaction. After stopping the reaction, the sample was centrifuged to collect the supernatant. The product was analyzed by HPLC under the conditions as shown below. HPLC conditions: Eluent A, 0.1% TFA; Eluent B, 90% acetonitrile, 0.08% TFA; analytical column, Develosil C30-UG-5 (4.6×150 mm, NOMURA CHEMICAL); flow rate, 1 ml/min; separation mode, 0 min-5% B, 20 min-50% B, 20.5 min-5% B, 25 min-5% B Hydrolysis Activity A reaction solution (100 µl, 5 mM maltotetraose, 20 mM $KH_2PO_4$—KOH (pH 6.0), enzyme solution) was reacted at 35° C. for 15 minutes, followed by thermal treatment (100° C., 5 min) to stop the reaction. After stopping the reaction, the sample was centrifuged to collect the supernatant. The product was analyzed by HPLC under the conditions as shown below. HPLC conditions: Eluent, 68% acetonitrile; analytical column, SUPELCOSIL LC-$NH_2$ (5 µm, 4.6×250 mm, SUPELCO); flow rate, 1 ml/min; separation mode, isocratic Temperature Stability Analysis:

The enzyme solution (±10 mM epigallocatechin gallate) was treated at different temperatures ranging from 20° C. to 60° C. for 1 hr, and then cooled to 4° C. To the cooled samples, 10 mM epigallocatechin gallate and 10 mg dextrin were added and reacted (different temperatures, pH 5.3, 24 hr). After addition of 0.5% TFA to stop the reaction, each sample was analyzed by reversed-phase HPLC.

Figure 10:
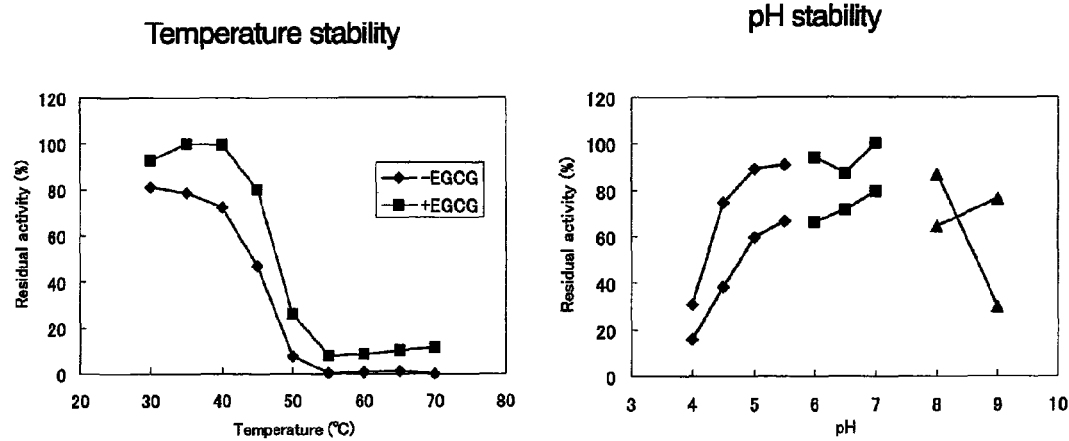
FIG. 10 is graphs showing the temperature stability and pH stability of TRa2.

The results obtained are shown in FIG. 10 (left).

pH Stability Analysis:

To the enzyme solution (±10 mM epigallocatechin gallate), a buffer of different pH (pH 4, 4.5, 5, Acetate-NaOH; pH 5.5, 6, 6.5, 7, NaH$_2$PO$_4$—NaOH; pH 8, 9, Tris-HCl) was added at a final concentration of 167 mM. After treatment at 4° C. for 16 hr, Acetate-NaOH (pH 5.3) was added at a final concentration of 400 mM. To the treated samples, 10 mM epigallocatechin gallate and 10 mg dextrin were added and reacted (45° C., different pH, 24 hr). After addition of 0.5% TFA to stop the reaction, each sample was analyzed by reversed-phase HPLC. The Acetate-NaOH concentration was 200 mM in reaction solution during activity measurement.

The results obtained are shown in FIG. 10 (right).

Figure 11:
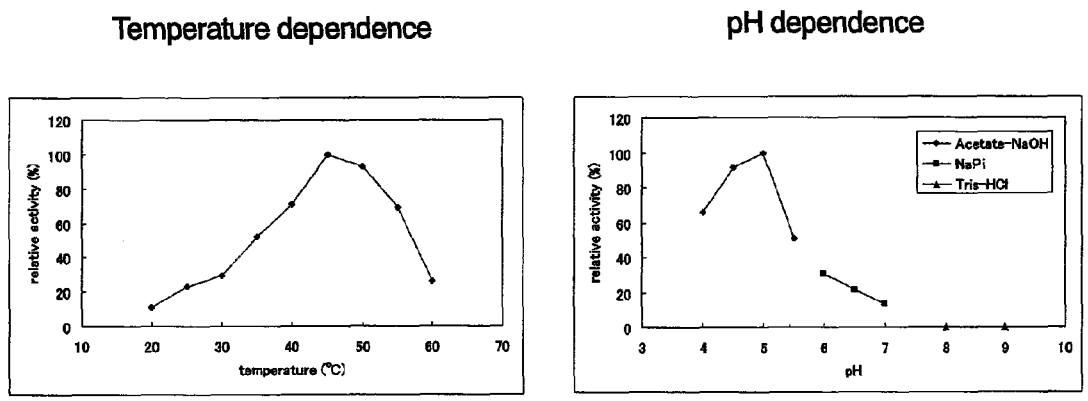
FIG. 11 is graphs showing the temperature dependence and pH dependence of TRa2-catalyzed carbohydrate hydrolysis reaction.

Analysis of Reaction Temperature Dependence:

The enzyme was added to 5 mM maltotetraose to perform hydrolysis reaction (different temperatures ranging from 20° C. to 60° C., pH 6.0, 15 min). After stopping the reaction at 100° C. for 5 min, each sample was analyzed by normal phase HPLC. The results obtained are shown in FIG. 11 (left).

Figure 12:
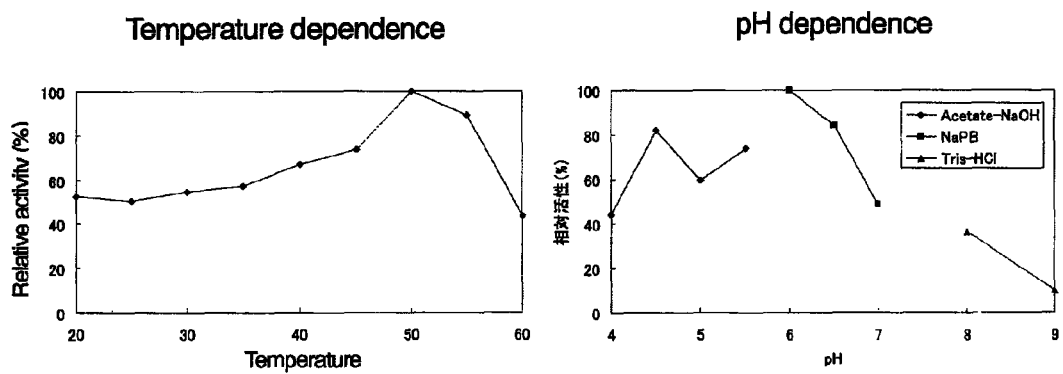
FIG. 12 is graphs showing the temperature dependence and pH dependence of TRa2-catalyzed glycosylation reaction.

In addition, the enzyme was added to 10 mM catechin and 10 mg dextrin to perform glycosyltransferase reaction (different temperatures ranging from 20° C. to 60° C., pH 5.3, 24 hr). After addition of TFA to stop the reaction, each sample was analyzed by reversed-phase HPLC. The results obtained are shown in FIG. 12 (left).

Analysis of Reaction pH Dependence:

The enzyme was added to 5 mM maltotetraose to perform hydrolysis reaction in a buffer of different pH (35° C., pH 4, 4.5, 5, Acetate-NaOH; pH 5.5, 6, 6.5, 7, NaH$_2$PO$_4$—NaOH; pH 8, 9, Tris-HCl, 15 min). After stopping the reaction at 100° C. for 5 min, each sample was analyzed by normal phase HPLC. The results obtained are shown in FIG. 11 (right).

In addition, the enzyme was added to 10 mM catechin and 10 mg dextrin to perform glycosyltransferase reaction (45° C., pH 4, 4.5, 5, Acetate-NaOH; pH 5.5, 6, 6.5, 7, NaH$_2$PO$_4$—NaOH; pH 8, 9, Tris-HCl, 24 hr). After addition of TFA to stop the reaction, each sample was analyzed by reversed-phase HPLC. The results obtained are shown in FIG. 12 (right).

Example 15

Characterization of Glycoside

Figure 13:
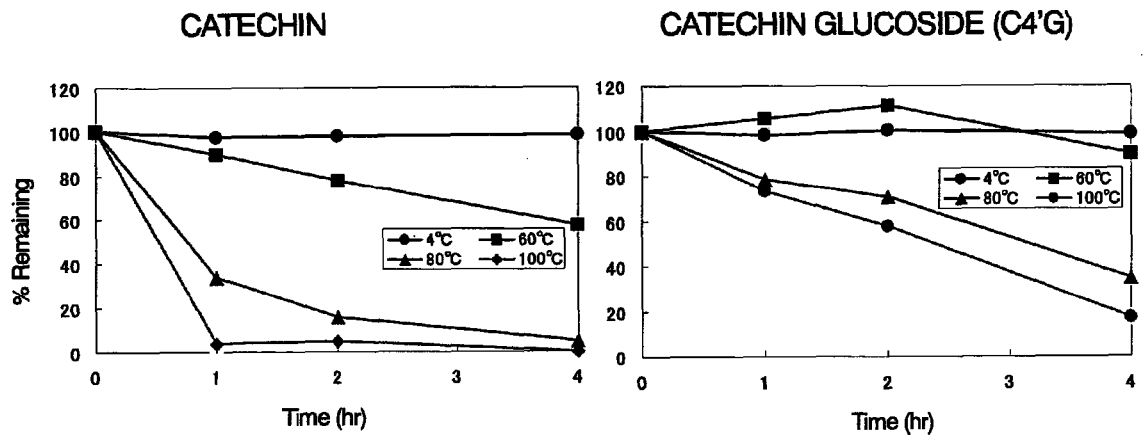
FIG. 13 is a graph showing the % remaining of (+)-catechin or 4'-O-α-D-glucopyranosyl-(+)-catechin after a solution containing the same was treated at different temperatures ranging from 4° C. to 100° C. for 0 to 4 hours.

Heat Stability:

After 10 mM potassium phosphate buffer (pH 7.0, 30 μl) containing 100 μM (+)-catechin or 4'-O-α-D-glucopyranosyl-(+)-catechin was treated at different temperatures ranging from 4° C. to 100° C. for 0 to 4 hours, each sample was transferred on ice and mixed with 0.1% TFA (60 μl), followed by HPLC analysis in the same manner as shown in Example 1. FIG. 13 shows the % remaining of (+)-catechin or 4'-O-α-D-glucopyranosyl-(+)-catechin when treated at different temperatures. The results indicated that 4'-O-α-D-glucopyranosyl-(+)-catechin was more stable against heat than catechin.

Figure 14:
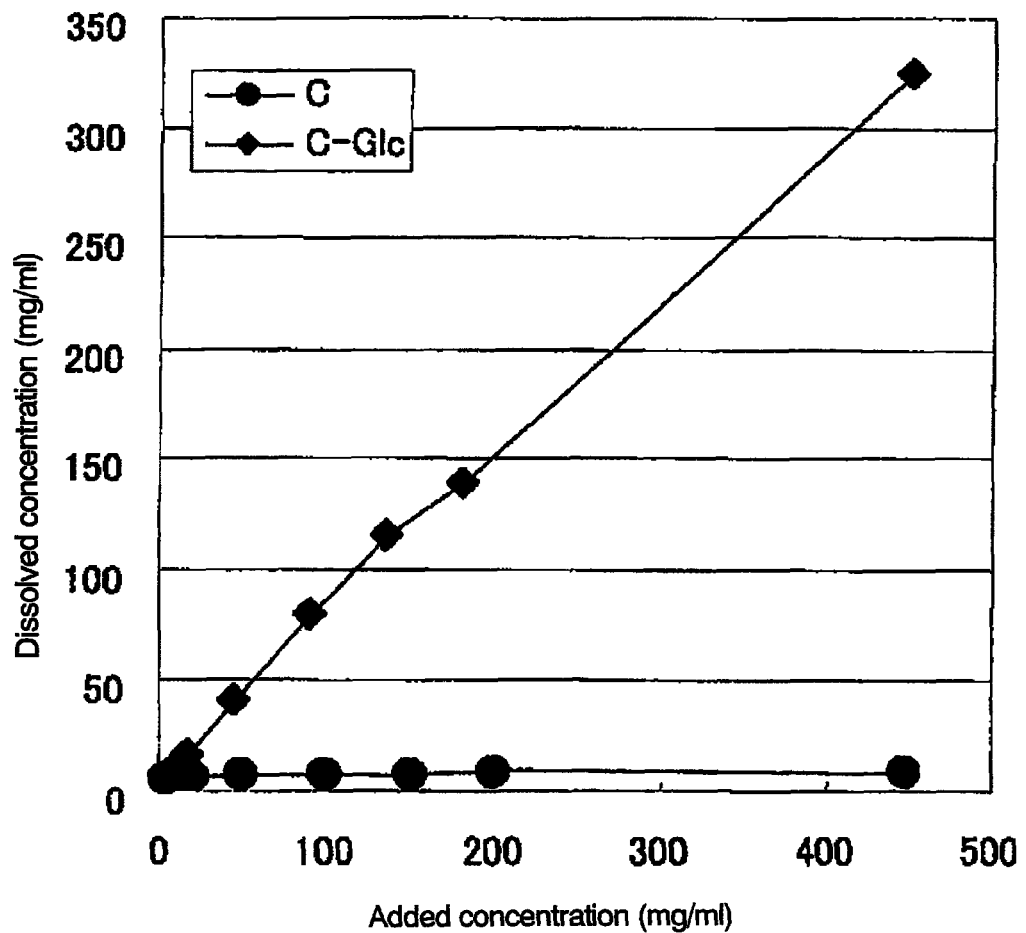
FIG. 14 is a graph showing the solubility of (+)-catechin and 5-O-α-D-glucopyranosyl-(+)-catechin in water.

Solubility:

(+)-Catechin or 5-O-α-D-glucopyranosyl-(+)-catechin was added to water at different concentrations ranging from 10 to 450 mg/ml and dissolved by vigorous stirring, followed by centrifugation to remove precipitates. The supernatant was analyzed by HPLC to quantify the amounts of (+)-catechin and 5-O-α-D-glucopyranosyl-(+)-catechin. The results obtained are shown in FIG. 14. The results indicated that (+)-catechin was substantially insoluble in water, whereas 5-O-α-D-glucopyranosyl-(+)-catechin showed at least 40-fold or higher solubility.

Industrial Applicability

The novel enzyme genes or modified variants thereof, transformants carrying the same, and novel enzyme proteins or modified variants thereof, which are obtained by the present invention, are useful in producing glycosides of flavonoid compounds or in producing foods, drugs and/or cosmetics based on such glycosides.

The invention claimed is:

1. An isolated polynucleotide comprising a polynucleotide selected from the group consisting of:
(A) a polynucleotide consisting of the nucleotide sequence of SEQ ID NO:6;
(B) a polynucleotide consisting of the nucleotide sequence of SEQ ID NO:6, except 1 to 9 nucleotides are substituted, deleted, inserted, and/or added, wherein the polynucleotide encodes a protein having flavonoid glycosylation activity;
(C) a polynucleotide consisting of the nucleotide sequence of SEQ ID NO:25;
(D) a polynucleotide consisting of the nucleotide sequence of SEQ ID NO:9;
(E) a polynucleotide consisting of the nucleotide sequence of SEQ ID NO:9, except 1 to 9 nucleotides are substituted, deleted, inserted, and/or added, wherein the polynucleotide encodes a protein having flavonoid glycosylation activity;
(F) a polynucleotide encoding a protein consisting of the amino acid sequence of SEQ ID NO:10;
(G) a polynucleotide encoding a protein consisting of the amino acid sequence of SEQ ID NO:10, except 1 to 9 amino acids are substituted, deleted, inserted, and/or added, wherein the encoded protein has flavonoid glycosylation activity; and
(H) a polynucleotide encoding a protein consisting of an amino acid sequence having at least 90% amino acid sequence identity to the amino acid sequence of SEQ ID NO:10, wherein the encoded protein has flavonoid glycosylation activity.

2. An isolated polynucleotide comprising a polynucleotide selected from the group consisting of:
(a) a polynucleotide consisting of the nucleotide sequence of SEQ ID NO:25;
(b) a polynucleotide consisting of the nucleotide sequence of SEQ ID NO:25, except 1 to 9 nucleotides are substituted, deleted, inserted, and/or added, wherein the polynucleotide encodes a protein having flavonoid glycosylation activity;
(c) a polynucleotide encoding a protein consisting of the amino acid sequence of SEQ ID NO:26;
(d) a polynucleotide encoding a protein consisting of the amino acid sequence of SEQ ID NO:26, except 1 to 9 amino acids are substituted, deleted, inserted, and/or added, wherein the encoded protein has flavonoid glycosylation activity; and
(e) a polynucleotide encoding a protein consisting of an amino acid sequence having at least 90% amino acid sequence identity to the amino acid sequence of SEQ ID NO:26, wherein the encoded protein has flavonoid glycosylation activity.

3. A vector comprising the polynucleotide according to claim 1.

4. An isolated transformant transformed with the vector according to claim 3.

5. An isolated polynucleotide comprising the nucleotide sequence of SEQ ID NO:14.

* * * * *